United States Patent
Nichols et al.

(10) Patent No.: US 12,398,093 B2
(45) Date of Patent: Aug. 26, 2025

(54) COMPOUNDS AND METHODS FOR TREATING INFLAMMATORY DISORDERS

(71) Applicant: Board of Supervisors of Louisiana State University and Agricultural and Mechanical College, Baton Rouge, LA (US)

(72) Inventors: Charles D. Nichols, New Orleans, LA (US); Gerald Billac, New Orleans, LA (US); David E. Nichols, Chapel Hill, NC (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 889 days.

(21) Appl. No.: 17/603,091

(22) PCT Filed: Apr. 13, 2020

(86) PCT No.: PCT/US2020/027981
§ 371 (c)(1),
(2) Date: Oct. 12, 2021

(87) PCT Pub. No.: WO2020/210823
PCT Pub. Date: Oct. 15, 2020

(65) Prior Publication Data
US 2022/0119340 A1    Apr. 21, 2022

Related U.S. Application Data

(60) Provisional application No. 62/833,140, filed on Apr. 12, 2019.

(51) Int. Cl.
*A61P 37/06* (2006.01)
*A61K 31/137* (2006.01)
*C07C 217/56* (2006.01)

(52) U.S. Cl.
CPC .......... *C07C 217/56* (2013.01); *A61K 31/137* (2013.01); *A61P 37/06* (2018.01)

(58) Field of Classification Search
CPC ................ C07C 217/56; A61P 37/06
See application file for complete search history.

(56) References Cited

U.S. PATENT DOCUMENTS

| | | |
|---|---|---|
| 2010/0016280 A1 | 1/2010 | Nichols et al. |
| 2015/0025063 A1 | 1/2015 | Caron et al. |
| 2015/0216799 A1 | 8/2015 | Farber |
| 2018/0055791 A1 | 3/2018 | Nichols et al. |

FOREIGN PATENT DOCUMENTS

| | | | |
|---|---|---|---|
| WO | 2014028796 A2 | 2/2014 | |
| WO | WO-2018204354 A1 * | 11/2018 | ........... A61K 31/137 |
| WO | 2019064031 A1 | 4/2019 | |

OTHER PUBLICATIONS

Altun et al. Electron-conformational study for the structureahallucinogenic activity relationships of phenylalkylamines, Bioorganic & Medicinal Chemistry, Sep. 2003, pp. 3861-3868. (Year: 2003)*

Altun et al. Electron-Conformational Study for the Structure-Hallucinogenic Activity Relationships of Phenylalkylamines. Bioorganic & Medicinal Chemistry 11 (2003) 3861-3868.

Auld et al. Receptor Binding Assays for HTS and Drug Discovery. In: Assay Guidance Manual [Internet]. Bethesda (MD): Eli Lilly & Company and the National Center for Advancing Translational Sciences; May 1, 2021, 42 pages.

Billac et al. Elucidating Anti-Inflammatory Signaling Paradigm at the 5-HT2A Receptor. FASEB Journal, Pharmacology, Publiahed online Apr. 1, 2019, 2 pages.

Braden et al. Molecular Interaction of Serotonin 5-HT2A Receptor Residues Phe339(6.51) and Phe340(6.52) with Superpotent N-Benzyl Phenethylamine Agonists. Mol. Pharmacol. 2006, 70(6): 1956-1964.

Chung et al. In Vitro and In Vivo Assessment of ADME and PK Properties During Lead Selection and Lead Optimization— Guidelines, Benchmarks and Rules of Thumb. 2015; In: Sittampalam et al. Assay Guidance Manual [Internet]. Bethesda (MD): Eli Lilly & Company and the National Center for Advancing Translational Sciences; created: Sep. 9, 2015, 14 pages.

Flanagan et al. Structure-Activity Relationship Analysis of Psychedelics in a Rat Model of Asthma Reveals the Anti-Inflammatory Pharmacophore. ACS Pharmacol Transl Sci. Aug. 13, 2020;4(2):488-502.

Hayes, Sh. Remington: The Science and Practice of Pharmacy, vol. I and vol. II. Twenty-second edition (review). J Med Libr Assoc. Jul. 2014; 102(3): 220-221.

International Search Report for PCT/US2020/027981 mailed Jun. 19, 2020, 4 pages.

Johnson et al., "[125I]-2-(2,5-Dimethoxy-4-Iodophenyl) aminoethane ([125I]-2C-I) as a label for the 5-HT2 receptor in rat frontal cortex." Pharmacol. Biochem. Behav. 1990, 35(1):211-7.

Kroeze et al. PRESTO-TANGO: an open-source resource for interrogation of the druggable human GPCR-ome. Nat. Struct. Mol. Biol. 2015, 22: 362-369.

Nau et al. Serotonin 5-HT2 receptor activation prevents allergic asthma in a mouse model. Am. J. Physiol. Lung Cell Mol. Physiol. 2015, 308(2): L191-L198. , 308(2): L191-L198.

Nichols et al. 1-(2,5-Dimethoxy-4-(trifluoromethyl)phenyl)-2-aminopropane: A Potent Serotonin 5-HT2A/2C Agonist. J. Med. Chem. 1994, 37, 25, 4346-4351.

(Continued)

*Primary Examiner* — Sarah Pihonak
*Assistant Examiner* — Mikhail O'Donnel Robinson
(74) *Attorney, Agent, or Firm* — Baker, Donelson, Bearman, Caldwell & Berkowitz, PC

(57) ABSTRACT

The invention features compounds and pharmaceutical compositions having anti-inflammatory properties. Also provided are methods of using the compounds or compositions of the invention for treating an inflammatory disorder in a subject in need thereof.

18 Claims, 18 Drawing Sheets

(56) References Cited

OTHER PUBLICATIONS

Nichols, D.E. Structure—activity relationshipsof serotonin 5-HT2Aagonists. WIREs Membr. Transp. Signal 2012, 1:559-579.
Oberlender et al. Substituent branching in phenethylamine-type hallucinogens: a comparison of 1-[2,5-dimethoxy-4-(2-butyl)phenyl]-2-aminopropane and 1-[2,5-dimethoxy-4-(2-methylpropyl)phenyl]-2-aminopropane. J. Med. Chem. 1984, 27(6), 788-792 (p. 16).
Stella et al., "Prodrugs: A Chemical Approach to Targeted Drug Delivery," Directed Drug Delivery, Borchardt et al., (ed.), pp. 247-267, Humana Press (1985).
Swarbrick et al. (editors). Encyclopedia of Pharmaceutical Technology, 1988-1999, Marcel Dekker, New York, part 1, 170 pages.
Swarbrick et al. (editors). Encyclopedia of Pharmaceutical Technology, 1988-1999, Marcel Dekker, New York, part 2, 160 pages.
Swarbrick et al. (editors). Encyclopedia of Pharmaceutical Technology, 1988-1999, Marcel Dekker, New York, part 3, 5 pages.
Wilman, "Prodrugs in Cancer Chemotherapy" Biochemical Society Transactions, 14, pp. 375-382, 615th Meeting Belfast (1986).
Written Opinion for PCT/US2020/027981 mailed Jun. 19, 2020, 4 pages.
Beuerle, G. et al. Three-dimensional Quantitative Structure-Activity Relationships of Hallucinogenic Phenylalkanamine and Tryptamine Derivatives: Studies using Comparative Molecular Field Analysis (CoMFA). Quantitative Structure-Activity Relationships, 16(6), pp. 447-458 (1997).
Clare, B. W. Structure-Activity Correlations for Psychotomimetics. 1. Phenylalkylamines: Electronic, Volume, and Hydrophobicity Parameters. J. Med. Chem., 33(2), pp. 687-702 (1990).

\* cited by examiner

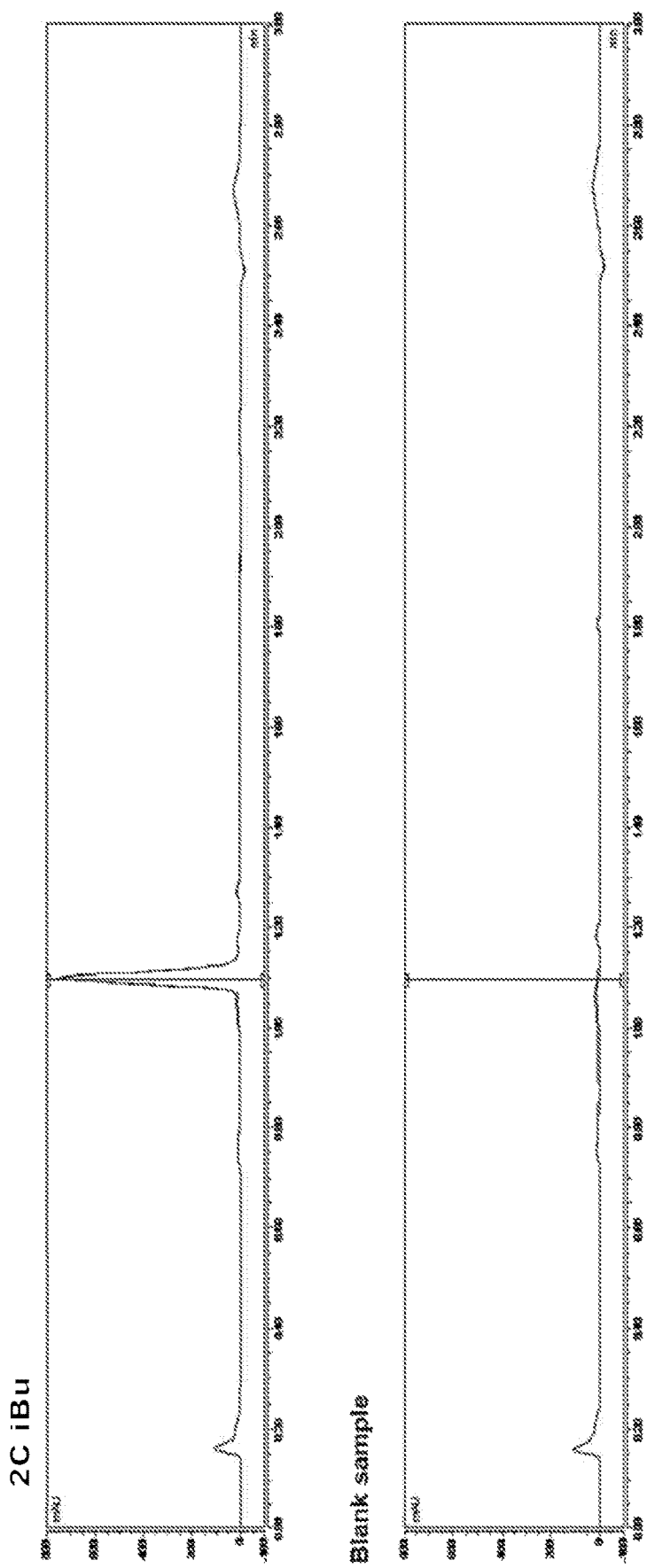
FIG. 1B – CONT.

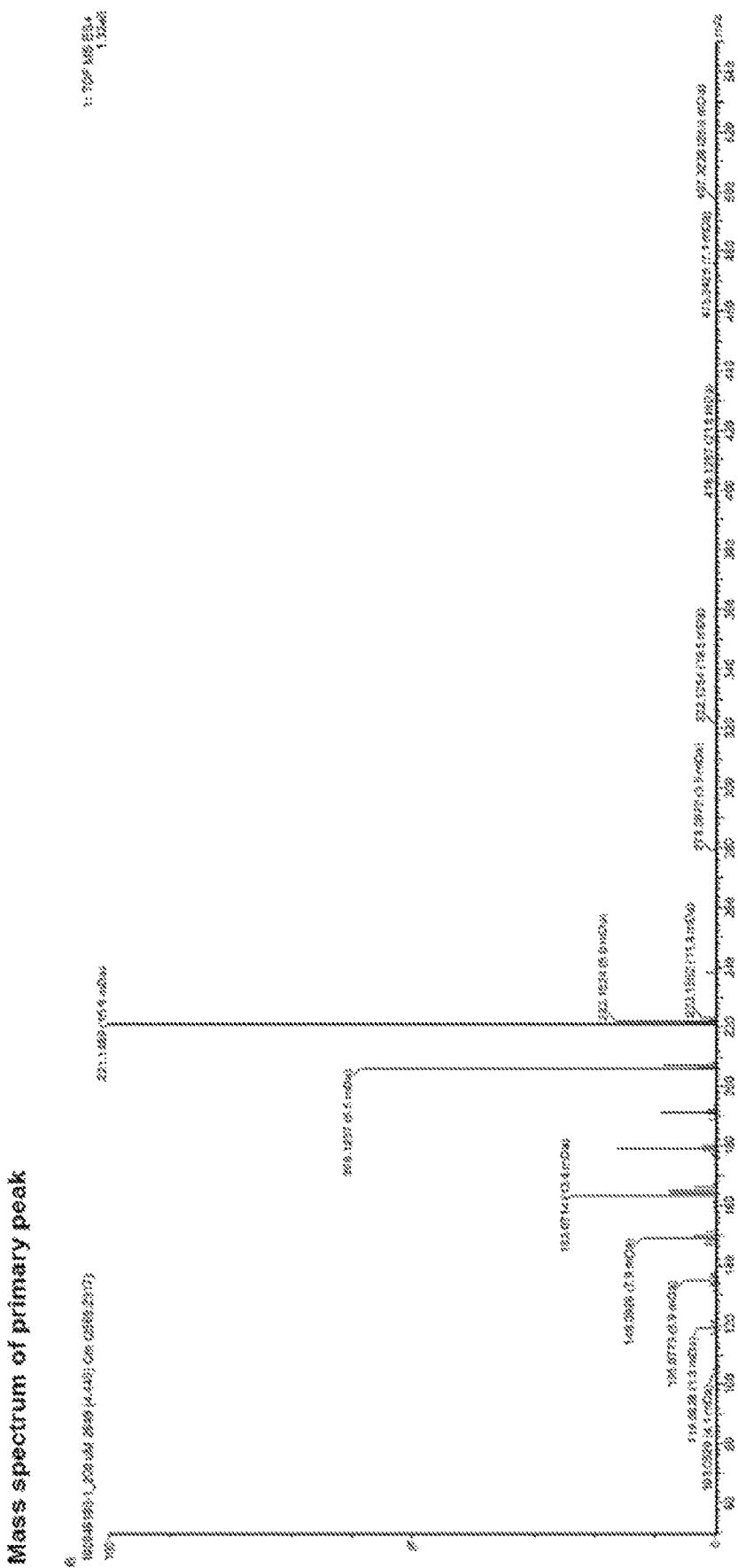
FIG. 1C – CONT.

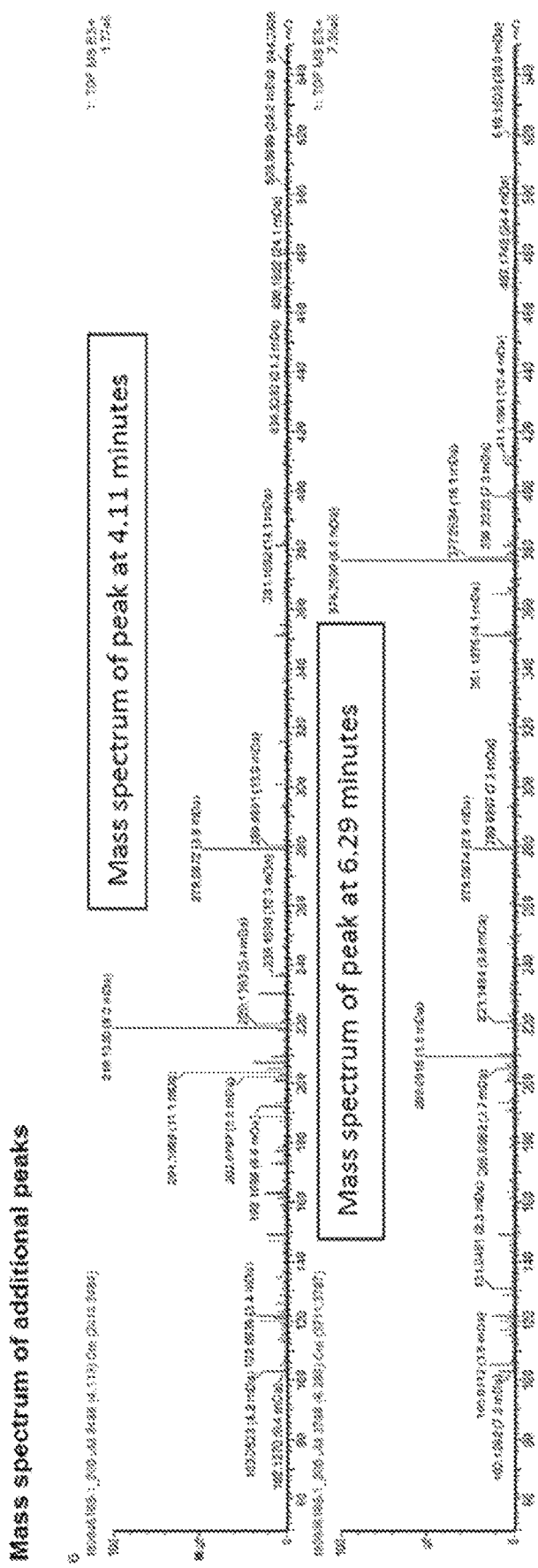
FIG. 1C – CONT.

COMPOUNDS AND METHODS FOR TREATING INFLAMMATORY DISORDERS

This application claims the benefit of U.S. Provisional Patent Application No. 62/833,140, filed Apr. 12, 2019, the entire contents of which are incorporated by reference herein in its entirety.

FIELD OF THE INVENTION

In general, the invention features compositions and methods for treating inflammatory disorders.

BACKGROUND OF THE INVENTION

Inflammation is a natural and necessary physiological process that occurs upon an organism's exposure to a foreign stimulus, such as a pathogen. However, inflammatory signaling can sometimes be misdirected and can occur in the absence of a legitimate threat to the organism. Such aberrant inflammatory signaling can cause damage to host cell tissue and can lead to a variety of long-term complications. Currently, key pathways of inflammation, such as TNF-α signaling, are being targeted using biologic drugs, such as monoclonal antibodies (infliximab and adalimumab) and soluble TNF-α receptor (etanercept).

However, there is a need in the field for development of small molecule anti-inflammatory compounds, e.g., for treatment of inflammatory conditions.

SUMMARY OF THE INVENTION

The present invention discloses compounds and pharmaceutical compositions that have potent anti-inflammatory properties. Also provided are methods of using the compounds or compositions of the invention, e.g., for treating an inflammatory disorder in a subject in need thereof.

An aspect of the invention features a compound of formula (X):

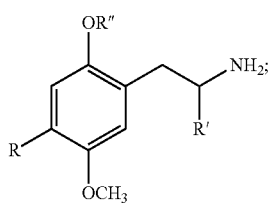

(X)

or a pharmaceutically acceptable acid addition salt (e.g., a hydrochloric acid salt) or prodrug thereof, wherein R' can be H or $CH_3$; and R" can be H or $CH_3$. In particular embodiments, R' can be H. In other embodiments, R' can be $CH_3$ (e.g., in the R stereochemistry). In some embodiments, R" can be H. In yet further embodiments, R can be a small branched alkyl group (e.g., $—CH(CH_3)_2$, $—C(CH_3)_3$, or $—CH(CH_2)_2$);

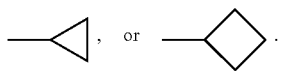

In some embodiments, if R is

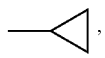

it may optionally be substituted with one or more $CH_3$ groups including all stereoisomers (for example,

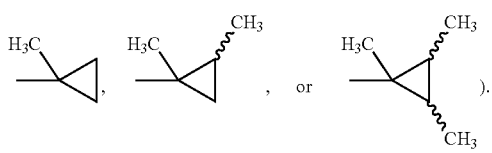

In some embodiments, if R is

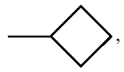

it may optionally be substituted with one or more $CH_3$ groups including all stereoisomers (for example,

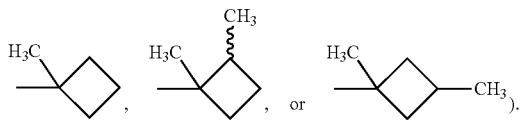

An aspect of the invention features a compound of formula (Y):

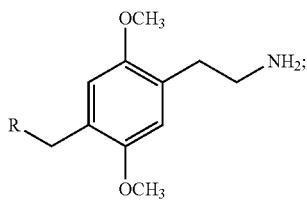

(Y)

or a pharmaceutically acceptable acid addition salt (e.g., a hydrochloric acid salt) or prodrug thereof, wherein R can be $CH(CH_3)_2$, $C(CH_3)_3$, $CH(CH_2)_2$);

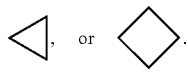

In one aspect, the invention features a compound of formula (I):

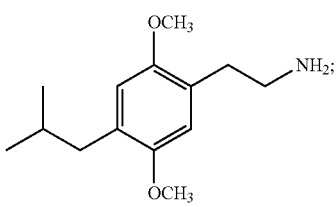

or a pharmaceutically acceptable acid addition salt (e.g., a hydrochloric acid salt) or prodrug thereof.

In another aspect, the invention features a compound of formula (II):

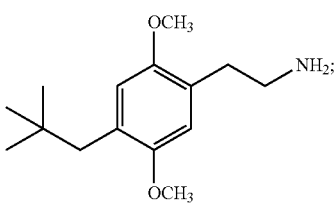

or a pharmaceutically acceptable acid addition salt (e.g., a hydrochloric acid salt) or prodrug thereof.

In yet another aspect, the invention features a compound of formula (III):

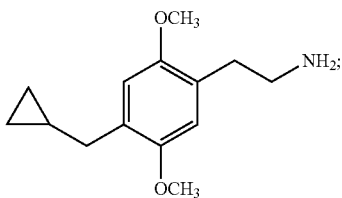

or a pharmaceutically acceptable acid addition salt (e.g., a hydrochloric acid salt) or prodrug thereof.

In another aspect, the invention includes a composition of any of the preceding aspects (e.g., a compound of formula (I), (II), or (III)) or an acid addition salt or prodrug thereof, and a pharmaceutically acceptable excipient. Such a pharmaceutical composition can be formulated for oral, intranasal, or pulmonary administration.

In another aspect, provided herein is a method of treating an inflammatory disorder in a subject in need thereof, the method including administering to the subject a therapeutically effective amount of the compound or the pharmaceutical composition of any of the preceding aspects. In some embodiments, the compound is administered in an amount resulting in circulating drug plasma levels of less than 20 ng/mL (e.g., 0.05 to 20 ng/mL, e.g., 0.1 to 15 ng/mL, 0.5 to 10 ng/mL, or 1 to 5 ng/mL, e.g., 0.05 to 0.1 ng/mL, 0.1 to 0.2 ng/mL, 0.2 to 0.3 ng/mL, 0.3 to 0.4 ng/mL, 0.4 to 0.5 ng/mL, 0.5 to 1.0 ng/mL, 1.0 to 5 ng/mL, 5 to 10 ng/mL, 10 to 15 ng/mL, or 15 to 20 ng/mL, e.g., about 0.05 ng/mL, 0.1 ng/mL, 0.2 ng/mL, 0.5 ng/mL, 1.0 ng/mL, 2.0 ng/mL, 2.5 ng/mL, 5.0 ng/mL, 7.5 ng/mL, 10 ng/mL, 12 ng/mL, 15 ng/mL, or 20 ng/mL). In some embodiments, the circulating drug plasma level of the compound is below the limit of detection (e.g., 0.1 ng/mL or less). In some embodiments, the amount of compound administered is 20 µg/kg body weight or less (e.g., less than 20 µg/kg, less than 15 µg/kg, less than 10 µg/kg, or less than 5 µg/kg body weight, e.g., from 1 to 20 µg/kg body weight, e.g., from 1 to 5 µg/kg, from 5 to 10 µg/kg, from 10 to 15 µg/kg, or from 15 to 10 µg/kg, e.g., about 5 µg/kg, about 10 µg/kg, about 15 µg/kg, or about 20 µg/kg). In some embodiments, the compound is administered at a frequency of one or multiple times per week (e.g., once per week, twice per week, three times per week, four times per week, five times per week, six times per week, seven times per week, or more, e.g., once daily, twice daily, three times daily, etc.). In some embodiments, the compound is administered intermittently, e.g., every other day, every other week, once per month, etc.

In some embodiments of any of the preceding embodiments or any of the methods described herein, the inflammatory disorder is asthma, chronic obstructive pulmonary disease, neuroinflammation, rheumatoid arthritis, atherosclerosis, psoriasis, type II diabetes, inflammatory bowel disease, Crohn's disease, multiple sclerosis, septicemia, or conjunctivitis.

In any of the methods provided herein, the compound can be administered by any suitable route of administration, e.g., orally, intranasally, or by inhalation. In some embodiments, the present compound or pharmaceutical composition thereof is administered by one or more of a variety of routes, including nasal, buccal, oral, by inhalation (e.g., as an oral spray, nebulizer, nasal spray, or aerosol), intravenous, intramuscular, intra-arterial, intramedullary, intrathecal, subcutaneous, intraventricular, transdermal, interdermal, rectal, intravaginal, intraperitoneal, topical (e.g., by powders, ointments, creams, gels, lotions, and/or drops), mucosal, enteral, vitreal, intratumoral, sublingual; by intratracheal instillation, bronchial instillation, and/or through a portal vein catheter. In some embodiments the composition is administered by systemic intravenous injection. In specific embodiments the composition is administered intravenously and/or orally.

Definitions

To facilitate the understanding of this invention, a number of terms are defined below and throughout the disclosure. Unless otherwise defined, all technical and scientific terms used herein have the same meaning as commonly understood by one of ordinary skill in the art to which this invention belongs. The terminology herein is used to describe specific embodiments of the invention, but their usage does not limit the invention, except as outlined in the claims.

As used herein, an "acid addition salt" refers to any pharmaceutically acceptable salt.

The term "prodrug" as used herein refers to an inactive precursor form of a pharmaceutically active substance that is capable of being enzymatically activated or converted into the more active parent form. See, for example, Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985).

As used herein, the term "pharmaceutically acceptable carrier" refers to an excipient or diluent in a pharmaceutical composition. For example, a pharmaceutically acceptable carrier may be a vehicle capable of suspending or dissolving the active compound (e.g., a composition described herein). The pharmaceutically acceptable carrier must be compatible with the other ingredients of the formulation and not deleterious to the recipient. In the present disclosure, the pharmaceutically acceptable carrier must provide adequate pharmaceutical stability to a compound described herein. The nature of the carrier differs with the mode of administration.

As used herein, the term "treat" or "treating" refers to administration of a compound or pharmaceutical composition for a therapeutic purpose. To "treat a disorder" or use for "therapeutic treatment" refers to administering treatment to a patient already suffering from a disease to ameliorate the disease or one or more symptoms thereof to improve the patient's condition (e.g., by reducing one or more symptoms of inflammation). The term "therapeutic" includes the effect of mitigating deleterious clinical effects of certain inflammatory processes (i.e., consequences of the inflammation, rather than the symptoms of inflammation). The methods of the invention can be used as a primary prevention measure, i.e., to prevent a condition or to reduce the risk of developing a condition. Prevention refers to prophylactic treatment of a patient who may not have fully developed a condition or disorder, but who is susceptible to, or otherwise at risk of, the condition. Thus, in the claims and embodiments, the methods of the invention can be used either for therapeutic or prophylactic purposes.

The term "administration" or "administering" refers to a method of giving a dosage of a compound or pharmaceutical composition to a subject.

The term "therapeutically effective amount," as used herein, refers to an amount, e.g., pharmaceutical dose, effective in inducing a desired effect in a subject or in treating a subject having a condition or disorder described herein (e.g., an inflammatory disorder). It is also to be understood herein that a "therapeutically effective amount" may be interpreted as an amount giving a desired therapeutic and/or preventative effect, taken in one or more doses or in any dosage or route, and/or taken alone or in combination with other therapeutic agents. For example, in the context of administering a composition described herein that is used for the treatment of a disorder or condition, an effective amount of a compound is, for example, an amount sufficient to prevent, slow down, or reverse the progression of the disorder or condition as compared to the response obtained without administration of the compound.

Terms such as "a", "an," and "the" are not intended to refer to only a singular entity, but include the general class of which a specific example may be used for illustration.

As used herein, the term "about" refers to a value that is within 10% above or below the value being described.

BRIEF DESCRIPTION OF THE FIGURES

The following Figures are illustrative of a particular embodiment of the present invention and are not limiting to various embodiments encompassed by the present invention.

DETAILED DESCRIPTION OF THE INVENTION

The present invention features 2C compounds having the structure of formulas (I), (II), and (III):

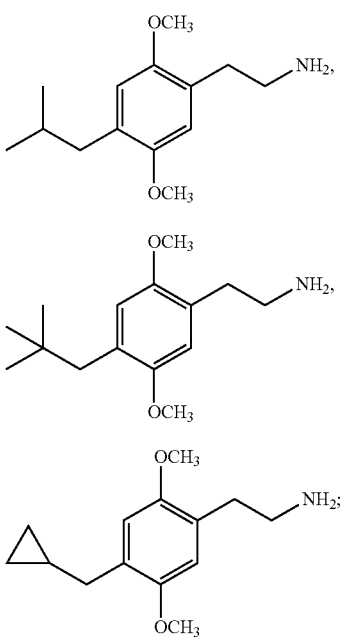

and acid addition salts and prodrugs thereof. Also provided herein are pharmaceutical compositions including said 2C compounds and methods of treatment using the compounds and pharmaceutical compositions, e.g., methods of treating an inflammatory disorder in a subject in need thereof.

I. Compounds

Hallucinogenic phenethylamines include compounds having an amphetamine structure with an alpha methyl on the side chain of the main ring. This class of compound is referred to as DOx, the structure of which is shown below, where R can be any suitable group (e.g., methyl, iodine, ethyl, etc.). Particular DOx compounds, such as the drug (R)-DOI, can be potent agonists of serotonin 5-HT$_2$ receptors.

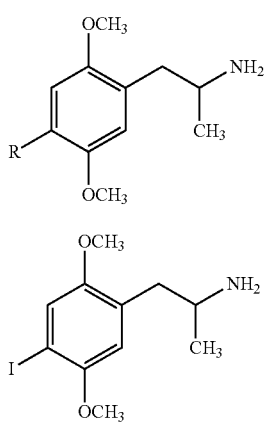

Figure 3:
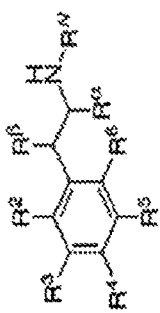
FIG. 3 is a structure-activity relationship table summarizing functional properties of various DOx and 2C compounds. *: Not efficacious (−), moderately efficacious (+), strongly efficacious (++); **: Data based on literature search conducted January 2019; (NT) Not Tested; (NR) Not Reported, i.e., insufficient publicly available characterization data.

Binding affinities of DOx compounds to the 5-HT$_2$ receptors are typically in the low nanomolar range (e.g., 0.1-10 nM; Nichols, *WIREs Membr. Transp. Signal* 2012, 1:559-579, incorporated herein by reference), and EC$_K$ values for effector pathway activation at the 5-HT$_{2A}$ receptor, such as the Gq pathway, can be in the low nanomolar range (e.g., 1-10 nM; FIG. 3).

A compound of a second class is referred to herein as a "2Cx compound," in reference to the absence of the side chain alpha methyl, compared to the DOx class. Thus, a 2C side chain includes two and only two carbon atoms (2C). Binding affinities of 2Cx compounds to the 5-HT$_2$ receptors are typically in the nanomolar range (e.g., 1-10 nM; Johnson et al., *Pharmacol. Biochem. Behav.* 1990, 35(1):211-7, incorporated herein by reference), and EC$_{50}$ values for effector pathway activation at the 5-HT$_{2A}$ receptor, such as the G1 pathway, can be in the low nanomolar range (e.g., 1-10 nM) and tend to show lower potency that their DOx counterparts (FIG. 3)

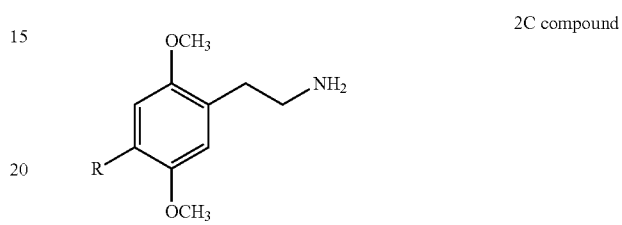

The present invention provides 2C compounds in which R is CH$_2$CH(CH$_3$)$_2$ (formula (I)), CH$_2$C(CH$_3$)$_3$ (formula (II)), or CH$_2$CH(CH$_2$)$_2$ (formula (III)):

The present invention is based, in part, on the discovery that these 2C compounds can have high potency for activation of the 5-HT$_{2A}$ receptor, high anti-inflammatory potency, but importantly, with generally lower potency in effecting behavior compared to DOx compounds. Thus, the compounds disclosed herein can provide anti-inflammatory efficacy without eliciting behavioral effects mediated by action in the central nervous system (CNS).

Also disclosed herein are pharmaceutically acceptable acid addition salts of these compounds and prodrugs thereof.

II. Pharmaceutical Compositions

Pharmaceutical Compositions of any of the aforementioned compounds (e.g., 2C compounds of formula (I), (II), or (III)) include tablets for oral use containing the compound in a mixture with non-toxic pharmaceutically acceptable excipients. These excipients may be, for example, inert diluents or fillers (e.g., sucrose, sorbitol, sugar, mannitol, microcrystalline cellulose, starches including potato starch, sodium chloride, or lactose); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

In some embodiments, the pharmaceutical composition is prepared, packaged, and/or sold in a formulation suitable for pulmonary administration, e.g., via the buccal cavity. Such a formulation may include dry particles that include the active ingredient, and which have a diameter in the range from about 0.5 nm to about 7 nm or from about 1 nm to about 6 nm. Such compositions are conveniently in the form of dry powders for administration using a device including a dry powder reservoir to which a stream of propellant may be directed to disperse the powder and/or using a self-propelling solvent/powder dispensing container such as a device including the active ingredient dissolved and/or suspended in a low-boiling propellant in a sealed container. Such powders include particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. The propellant may constitute 50% to 99.9% (w/w) of the composition, and active ingredient may constitute 0.1% to 20% (w/w) of the composition. A propellant may further include additional ingredients such as a liquid non-ionic and/or solid anionic surfactant and/or a solid diluent (which may have a particle size of the same order as particles including the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, including active ingredient, and may conveniently be administered using any nebulization and/or atomization device. Such formulations may further include one or more additional ingredients including, but not limited to, a flavoring agent such as saccharin sodium, a volatile oil, a buffering agent, a surface-active agent, and/or a preservative such as methylhydroxybenzoate. Droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder including the active ingredient and having an average particle from about 0.2 µm to 500 µm. Such a formulation is administered in the manner in which snuff is taken, i.e. by rapid inhalation through the nasal passage from a container of the powder held close to the nose.

Formulations suitable for nasal administration may, for example, include from about as little as 0.1% (w/w) and as much as 100% (w/w) of active ingredient, and may include one or more of the additional ingredients described herein. A pharmaceutical composition may be prepared, packaged, and/or sold in a formulation suitable for pulmonary administration. Alternately, formulations suitable for buccal administration may include a powder and/or an aerosolized and/or atomized solution and/or suspension including active ingredient. Such powdered, aerosolized, and/or aerosolized formulations, when dispersed, may have an average particle and/or droplet size in the range from about 0.1 nm to about 200 nm, and may further include one or more of any additional ingredients described herein.

Pharmaceutical compositions may be in the form of tablets and/or lozenges made using conventional methods, and may contain from 0.1% to 20% (w/w) active ingredient, the balance including an orally dissolvable and/or degradable composition and, optionally, one or more of the additional ingredients described herein. Tablets may be uncoated or they may be coated by known techniques, optionally to delay disintegration and absorption in the gastrointestinal tract and thereby providing a sustained action over a longer period. For example, the coating may be adapted to release the compound in a predetermined pattern (e.g., in order to achieve a controlled release formulation) or it may be adapted not to release the compound until after passage through the stomach. The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Additionally or alternatively, a time-delay material such as, e.g., glyceryl monostearate or glyceryl distearate may be incorporated in a tablet.

Solid tablet compositions may include a coating adapted to protect the compound from unwanted chemical changes, (e.g., chemical degradation prior to the release of the compound). The coating may be applied on the solid dosage form in a similar manner to that described in Encyclopedia of Pharmaceutical Technology (eds. J. Swarbrick and J. C. Boylan, 1988-1999, Marcel Dekker, New York).

Pharmaceutical compositions for oral use may also be presented as chewable tablets, or as hard gelatin capsules in which the compound is mixed with an inert solid diluent (e.g., potato starch, lactose, microcrystalline cellulose, calcium phosphate, or kaolin), or as soft gelatin capsules wherein the compound is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Powders, dispersible powders, or granules suitable for preparation of an aqueous suspension by addition of water are convenient dosage forms for oral administration of compounds. Formulation as a suspension provides the compound in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers, and adjuvants. The formulation and preparation of such compositions are well known to those skilled in the art of pharmaceutical formulation. Formulations can be found in Hayes (Remington: The Science and Practice of Pharmacy, volume I and volume II. Twenty-second edition. Philadelphia, 2012).

Compositions for parenteral use (e.g., intravenous administration) may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the compound (e.g., a compound having the structure of formula (I), (II), or (III)), the composition may include suitable parenterally acceptable carriers and/or excipients. The compound may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated herein, the pharmaceutical compositions according to the invention may be in a form suitable for sterile injection. To prepare such a composition, the compound is dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

III. Methods

Provided herein are methods of using a compound or pharmaceutical composition described herein to treat an inflammatory disorder in a subject. Methods of treating an inflammatory disorder include administering to a subject in need thereof a therapeutically effective amount of a compound or pharmaceutical composition of the invention. For example, methods of treating an inflammatory disorder include administration of a compound of the invention (e.g., a 2C compound having the structure of formula (I), (II), or (III), or an acid addition salt or prodrug thereof) or a pharmaceutical composition thereof. Alternatively, the methods herein provide treatment of an inflammatory disorder by administration of such a compound, or pharmaceutical composition thereof.

The exact amount of the compound or composition required for therapeutic effect can vary from subject to subject, depending on the species, age, weight, and general condition of the subject, the severity of the disease, the particular composition, its mode of administration, its mode of activity, and the like. Pharmaceutical compositions in accordance with the present disclosure are typically formulated in dosage unit form for ease of administration and uniformity of dosage. It will be understood, however, that the total daily usage of the compositions of the present disclosure will be decided by the attending physician within the scope of sound medical judgment. The specific therapeutically effective level for any particular subject will depend upon a variety of factors including the particular inflammatory disorder being treated and the severity thereof; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

In some embodiments of any of the methods described herein, the inflammatory disorder is asthma, chronic obstructive pulmonary disease, neuroinflammation, rheumatoid arthritis, atherosclerosis, psoriasis, type II diabetes, inflammatory bowel disease, Crohn's disease, multiple sclerosis, septicemia, or conjunctivitis.

Compositions described herein may be administered to subjects, such as human patients or, alternatively, to other mammals, such as domesticated animals, cats, dogs, mice, or rats.

Compositions described herein may be administered by any route. In some embodiments, the present compound or pharmaceutical composition thereof is administered by one or more of a variety of routes, including nasal, buccal, oral, by inhalation (e.g., as an oral spray, nasal spray, or aerosol), intravenous, intramuscular, intra-arterial, intramedullary, intrathecal, subcutaneous, intraventricular, transdermal, interdermal, rectal, intravaginal, intraperitoneal, topical (e.g., by powders, ointments, creams, gels, lotions, and/or drops), mucosal, enteral, vitreal, intratumoral, sublingual; by intratracheal instillation, bronchial instillation, and/or through a portal vein catheter. In some embodiments the composition is administered by systemic intravenous injection. In specific embodiments the composition is administered intravenously and/or orally.

A compound of the invention can be administered in a therapeutically effective amount (e.g., an amount that results in the desired therapeutic effect, e.g., within the therapeutic window between a dose sufficient to reduce inflammation and a dose that elicits a psychoactive effect (about a ten-fold difference)). In some embodiments, the compound is administered in an amount resulting in circulating drug plasma levels of less than 20 ng/mL (e.g., 0.05 to 20 ng/mL, e.g., 0.1 to 15 ng/mL, 0.5 to 10 ng/mL, or 1 to 5 ng/mL, e.g., 0.05 to 0.1 ng/mL, 0.1 to 0.2 ng/mL, 0.2 to 0.3 ng/mL, 0.3 to 0.4 ng/mL, 0.4 to 0.5 ng/mL, 0.5 to 1.0 ng/mL, 1.0 to 5 ng/mL, 5 to 10 ng/mL, 10 to 15 ng/mL, or 15 to 20 ng/mL, e.g., about 0.05 ng/mL, 0.1 ng/mL, 0.2 ng/mL, 0.5 ng/mL, 1.0 ng/mL, 2.0 ng/mL, 2.5 ng/mL, 5.0 ng/mL, 7.5 ng/mL, 10 ng/mL, 12 ng/mL, 15 ng/mL, or 20 ng/mL), e.g., in a human subject. In some embodiments, the circulating drug plasma level of the compound is below the limit of detection (e.g., 0.1 ng/mL or less). In some embodiments, a therapeutically effective amount of the compound can be less than about 20 µg/kg body weight (e.g., less than 20 µg/kg, less than 15 µg/kg, less than 10 µg/kg, or less than 5 µg/kg body weight, e.g., from 1 to 20 µg/kg body weight, e.g., from 1 to 5 µg/kg, from 5 to 10 µg/kg, from 10 to 15 µg/kg, or from 15 to 10 µg/kg, e.g., about 5 µg/kg, about 10 µg/kg, about 15 µg/kg, or about 20 µg/kg).

In certain embodiments, compositions in accordance with the present disclosure may be administered at dosage levels sufficient to deliver from about 0.0001 µg/kg to about 100 µg/kg, from about 0.01 µg/kg to about 50 µg/kg, from about 0.1 µg/kg to about 40 µg/kg, from about 0.5 µg/kg to about 30 µg/kg, from about 0.01 µg/kg to about 10 µg/kg, from about 0.1 µg/kg to about 10 µg/kg, or from about 1 µg/kg to about 25 µg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In some embodiments, the compound is administered at a frequency of one to three times per week (e.g., once per week, twice per week, three times per week, four times per week, five times per week, six times per week, seven times per week, or more, e.g., once daily, twice daily, three times daily, etc.). In some embodiments, the compound is administered intermittently, e.g., every other day, every other week, once per month, etc. In certain embodiments, the desired dosage may be delivered using multiple administrations (e.g., two, three, four, five, six, seven, eight, nine, ten, eleven, twelve, thirteen, fourteen, or more administrations).

Compositions described herein may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Pharmaceutical compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that improve their bioavailability, reduce and/or modify their metabolism, inhibit their excretion, and/or modify their distribution within the body.

It will further be appreciated that compounds or compositions utilized in combination may be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually.

EXAMPLES

The following examples are put forth so as to provide those of ordinary skill in the art with a description of how the compositions and methods claimed herein can be performed, made, and evaluated, and are intended to be purely exemplary of the invention and are not intended to limit the scope of what the inventor regards as his or her invention.

Example 1. Synthesis and Characterization of 2C-iBu

Figure 1A:
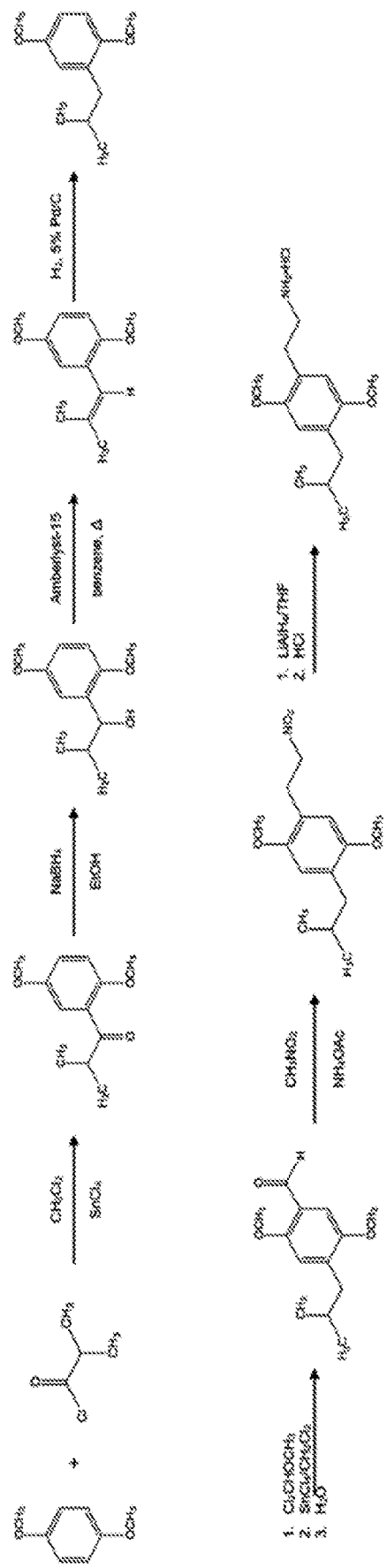
FIG. 1A is a diagram showing a synthesis of 2,5-dimethoxy-4-isobutylphenethylamine (2C-iBu).

Synthesis of 2C-iBu is a modification of the synthesis route for DOiBu as described in Oberlender et al., *J. Med. Chem.* 1984, 27(6), 788-792; incorporated herein by reference. Briefly, aldehyde 10 was treated with nitromethane and ammonium acetate to afford the corresponding nitroethene as bright yellow needles. Reduction of the nitroethene with a solution of LiAlH4 and standard workup resulted in the amine, which was converted to its hydrochloride salt and crystallized. This synthesis route is shown in FIG. 1A.

The purity of 2C-iBu was assessed using LCUV and LCMS analysis. A stock solution of 10 mM 2C-iBu in DMSO was diluted to 200 µM with 25% methanol/25% acetonitrile/50% H2O. A blank sample was prepared by diluting an equivalent volume of DMSO in the same fashion.

The dilute sample of 2C-iBu was analyzed by LCUV and LCMS using the following methods:

LCUV
    Mobile Phase A: 12 mM ammonium formate/6 mM formic acid in water
    Mobile Phase B: 6 mM ammonium formate/3 mM formic acid in water/acetonitrile (1/9, v/v)
    Column: Thermo DASH aQ C18, 3 micron, 2.1×20 mm (#25003-022150)
Gradient Program:

TABLE 1

| Time (min) | % B | Flow rate (mL/min) |
|---|---|---|
| 0 | 0 | 1.5 |
| 1.5 | 90 | 1.5 |
| 2.1 | 90 | 1.5 |
| 2.2 | 0 | 1.5 |
| 3.0 | 0 | 1.5 |

Detection with Dionex UltiMate 3000 Diode Array Detector
    Wavelength: UV-Vis_1: 205 nm+/−10 nm
    UV-Vis_2: 230 nm+/−10 nm
    UV-Vis_3: 260 nm+/−10 nm
    UV-Vis_4: 300 nm+/−10 nm
LCMS
    Mobile Phase A: 0.1% formic acid in water
    Mobile Phase B: 0.1% formic acid in acetonitrile
    Column: Acquity HSS T3, 1.8 micron, 2.1×100 mm (#186003539)
Gradient Program:

TABLE 2

| Time (min) | % B | Flow rate (mL/min) |
|---|---|---|
| 0 | 5 | 0.5 |
| 1.0 | 5 | 0.5 |

TABLE 2-continued

| Time (min) | % B | Flow rate (mL/min) |
|---|---|---|
| 7.0 | 95 | 0.5 |
| 7.5 | 95 | 0.5 |
| 8.0 | 5 | 0.5 |
| 10.0 | 5 | 0.5 |

Figure 1B:
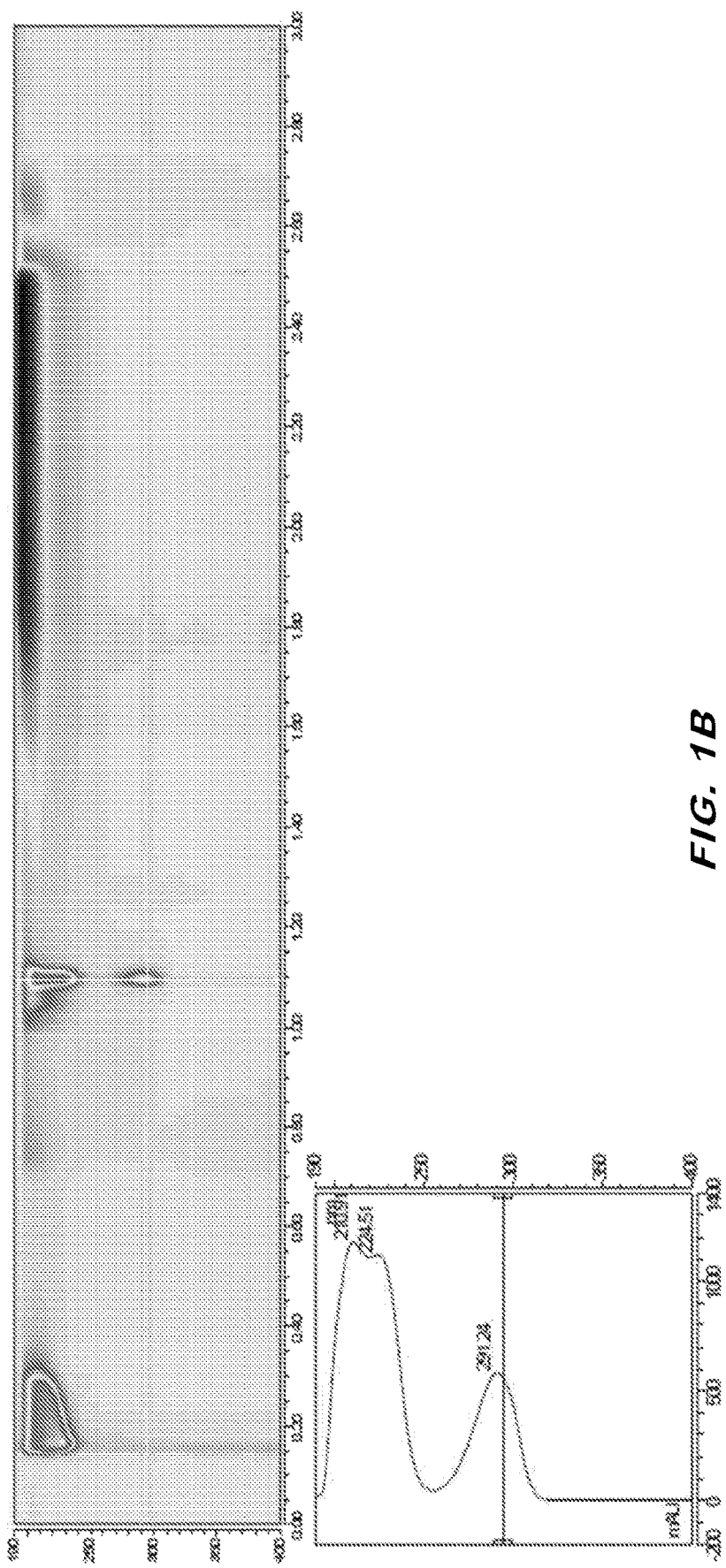
FIG. 1B is a set of graphs showing liquid chromatography-UV (LCUV) characterization of 2C-iBu.

Detection with Xevo G2 QTof (Waters) mass spectrometer
 Acquisition Method: Positive, Sensitivity Mode, $MS^E$
 Source temperature: 150° C.
 Desolvation temperature: 475° C.
 Capillary voltage: 1.5 kV
 Sampling Cone voltage: 125 V
 Extraction cone voltage: 7.0 V
 Cone gas: 100 L/h
 Desolvation gas: 500 L/h
 Mass range: 100-1000 Da FIG. 1B shows a single primary peak eluting at 1.1 minutes. One small additional peak eluting at 1.27 minutes appeared to be in the 2C-iBu chromatogram and was not observed in the blank sample; however, LCMS analysis did not indicate any significant analyte eluting later than the parent in the chromatogram.

Figure 1C:
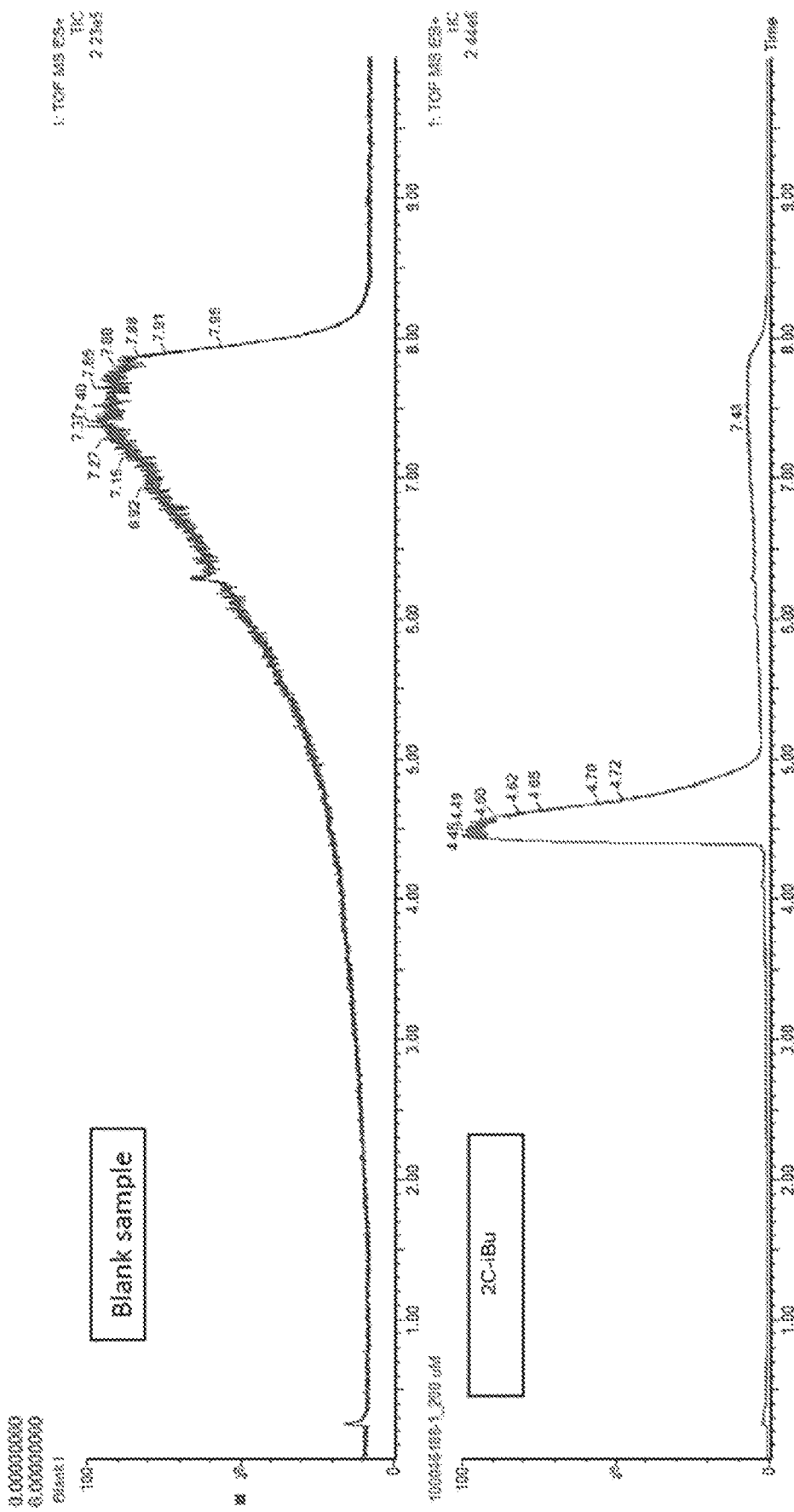
FIG. 1C is a set of graphs showing liquid chromatography-mass spectrometry (LCMS) characterization of 2C-iBu.

As shown in FIG. 1C, an earlier eluting peak at 4.11 minutes was observed in the LCMS chromatogram with a 219 m/z ion in the mass spectrum. The parent compound has an abundant precursor ion at 221 m/z which presumably occurs from loss of the amino group in the MS source. The peak at 4.11 minutes could represent an impurity two mass units less than the parent compound which fragments the same way. The conclusion is that 2C-iBu is >99% pure within the limits of detection of the methods used in this study.

Example 2. Receptor Pharmacology

HEK cells stably expressing the human 5-HT$_{2A}$ receptor (Braden et al., Mol. Pharmacol. 2006, 70(6): 1956-1964; incorporated herein by reference) were used to determine $EC_{50}$ and $E_{MAX}$ values for Gq-mediated calcium transients by 2C-iBu (Table 3) and other compounds (FIG. 3). Cells were seeded onto 96-well poly-D-lysine plates at ~50000 cells/well 24 hours prior to the experiment and cultured at 37° C. in Opti-MEM Reduced Serum Medium supplemented with 4% dialyzed fetal bovine serum. On the day of experiment, the cells were washed once with HBSS supplemented with 20 mM HEPES, loaded with 75 µL of 3 µM Fluo-4 AM (molecular probe) diluted in HBSS-HEPES buffer, incubated for 1.5 hours at room temperature, washed twice with HBSS-HEPES, and maintained in 50 µL HBSS-HEPES at 25° C. The plates of dye-loaded cells were placed into a FlexStation III microplate reader (Molecular Devices, LLC) to monitor fluorescence (excitation, 488 nm; emission, 525 nm; cutoff, 515 nm). Test compounds were added 30 seconds after the start of the scan at 2× concentration in 50 µL of HBSS-HEPES while monitoring fluorescence for an additional 200 seconds at 2-second intervals. After obtaining a calcium mobilization trace for each sample, calcium responses to test compounds were quantified as the percentage of change (peak fluorescence–baseline fluorescence level, denoted as ΔF) from baseline fluorescence level (denoted as F); ΔF/F (%). As controls, buffer alone signal accounted for baseline response and serotonin agonist peak signal accounted for 100% response. The bar graph and curving-fitting routines were carried out using Graph-Pad Prism 3.0 (GraphPad Software, Inc.).

To measure β-arrestin-2 recruitment by 2C-iBu, HTLA cells were transiently transfected with a 5-HT$_{2A}$R-Tango construct, as described in Kroeze et al. (Nat. Struct. Mol. Biol. 2015, 22: 362-369; incorporated herein by reference). Next, a PRESTO-Tango recruitment assay was performed by measuring luminescence as described in Kroeze et al. to determine $EC_{50}$ and $E_{MAX}$ values. Results are shown in Table 3, below.

TABLE 3

Receptor Pharmacology Summary

|  | Units | $Ca^{2+}$ | β-arrestin-2 |
|---|---|---|---|
| $EC_{50}$ | nM | $1.3 \times 10^{-9}$ | $5.75 \times 10^{-8}$ |
| $E_{MAX}$ | % of reference ligand serotonin | 103% | 77% |

Direct Comparison of DOx vs 2C Compounds 2C compounds were compared directly against DOx compounds in terms of calcium mobilization and recruitment of beta arrestin using the methods described above. Data was analyzed using GraphPad Prism software to determine $E_{MAX}$ as a percentage of 5-HT response, and $pEC_{50}$. Results are shown in Tables 4 and 5, below.

TABLE 4

Calcium Mobilization

|  | $E_{MAX}$ (%) | $pEC_{50}$ |  | $E_{MAX}$ (%) | $pEC_{50}$ |
|---|---|---|---|---|---|
| 5-HT | 100.00 | -8.39 |  |  |  |
|  |  |  | 2C-NP | 76.00 | -6.81 |
| DOiBu | 90.57 | -8.35 | 2C-iBu | 87.95 | -8.66 |
| R-DOB | 79.80 | -8.84 | 2C-B | 78.00 | -8.11 |
| R-DOI | 112.40 | -8.78 | 2C-I | 72.80 | -8.14 |
| R-2,5-DMA | 108.38 | -6.37 | 2C-H | 69.50 | -6.34 |
| DOiP | 73.17 | -8.29 | 2C-iP | 52.07 | -7.59 |

TABLE 5

Beta Arrestin Recruitment

|  | $E_{MAX}$ (%) | $pEC_{50}$ |  | $E_{MAX}$ (%) | $pEC_{50}$ |
|---|---|---|---|---|---|
| 5-HT | 100.00 | -6.70 |  |  |  |
|  |  |  | 2C-NP | * | * |
| DOiBu | 70.19 | -8.23 | 2C-iBu | 57.44 | -7.87 |
| R-DOB | 98.14 | -7.87 | 2C-B | 39.46 | -5.99 |
| R-DOI | 71.77 | -8.22 | 2C-I | * | * |
| R-2,5-DMA | 65.51 | -5.12 | 2C-H | 10.98 | -7.07 |
| DOiP | 20.40 | -8.24 | 2C-iP | 3.46 | -7.80 |

* No activity detected

Example 3. Allergic Asthma Model

A modification of the ovalbumin model of allergic asthma and whole body plethysmography protocol as described in Nau et al. (Am. J. Physiol. Lung Cell Mol. Physiol. 2015, 308(2): L191-L198; incorporated herein by reference) was used to determine ΔPenh, a measure of airways hyperresponsiveness (AHR), in response to methacholine challenge in adult male Brown Norway rats. Results, shown in FIGS. 2A-2G, represent PenH change measured in the ovalbumin allergic asthma assay in rats, with the exception of FIG. 2C, which was measured in mice, for nebulized inhaled drug. Statistics were performed using 2-way ANOVA with Tukey post hoc test for multiple comparisons.

Allergic asthma is defined as a chronic inflammatory disorder of the airways. This disease is characterized by airway inflammation, persistent airways AHR and intermittent, reversible airways obstruction. Chronic allergen exposure in rodent has been shown to reproduce some of the hallmarks of asthma including allergen-dependent sensitisation, a Th2-dependent allergic inflammation characterized by eosinophilic influx into the airway mucosa, and AHR.

Figure 2A:
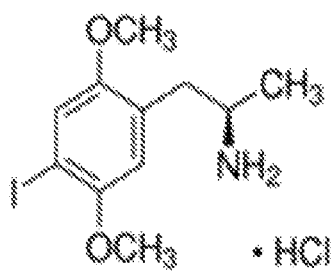
FIGS. 2A-2G are a series of graphs showing change in enhanced pause (ΔPenh) as a function of methacholine challenge in adult male Brown Norway rats, details of which are described in Example 3. Rats were untreated (naive; circles), treated with ovalbumin (OVA; squares), or treated with various experimental compounds in combination with OVA (triangles). Experimental compounds include R-DOI at 1.0 mg/kg (FIG. 2A; *$p<0.05$, significant difference from OVA to naive; #$p<0.05$ OVA vs. OVA+R-DOI), 25-I-NBOMe at 1.0 mg/kg (FIG. 2B; <0.05, significant difference from OVA to naive; #$p<0.05$, significant difference from OVA to OVA+25-I-NBOMe; ^$p<0.05$, significant difference from OVA+25-I-NBOMe to naive), DOB at 1.0 mg/kg (FIG. 2C; #$p<0.05$, significant difference from OVA to OVA+DOB; *$p<0.05$, significant difference from OVA to naive; ^$p<0.05$, significant difference from OVA+DOB to naive), 2C-B-Fly.HCl at 0.5 mg/kg (FIG. 2D; *$p<0.05$, significant difference from OVA to naive, and from 2C-B-Fly.HCl+ OVA to naive), 2CB2 at 0.5 mg/kg (FIG. 2E; #$p<0.05$, significant difference from OVA to OVA+TCB2; *$p<0.05$, significant difference from OVA to naive; ^$p<0.05$, significant difference from OVA+TCB2 to naive), DOTFM at 0.5 mg/kg (FIG. 2F; ^$p<0.05$, significant difference from OVA+DOTFM to naive), and 2C-iBu (FIG. 2G; *$p<0.05$, significant difference from OVA+2C-iBu.HCl to naive). The structure of each experimental compound is shown to the left of the corresponding graph.
Figure 2A:
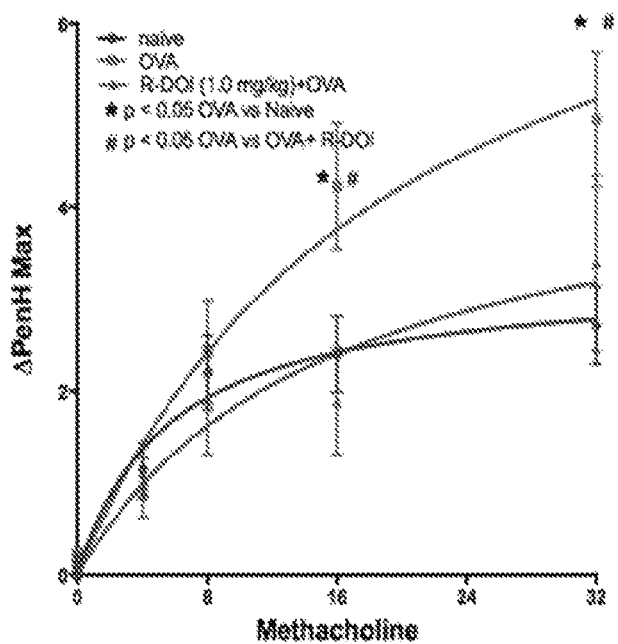
Figure 2B:
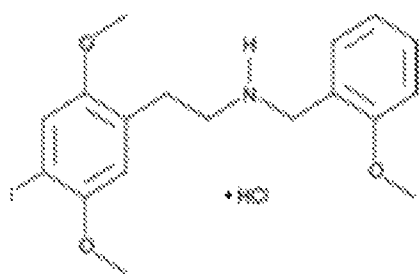
Figure 2B:
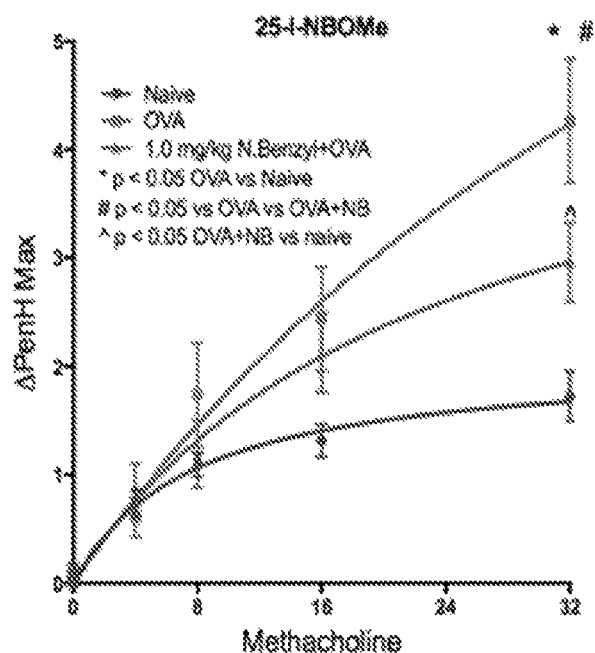
Figure 2C:
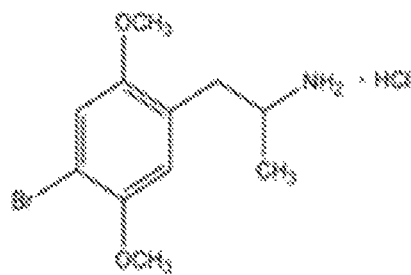
Figure 2C:
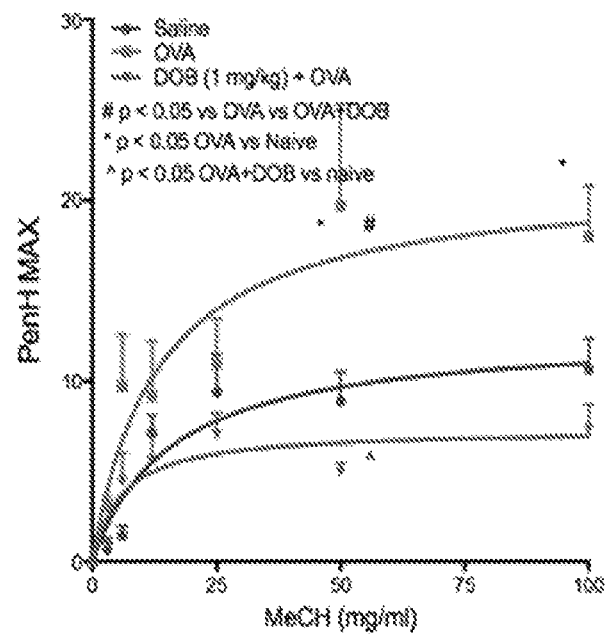
Figure 2D:
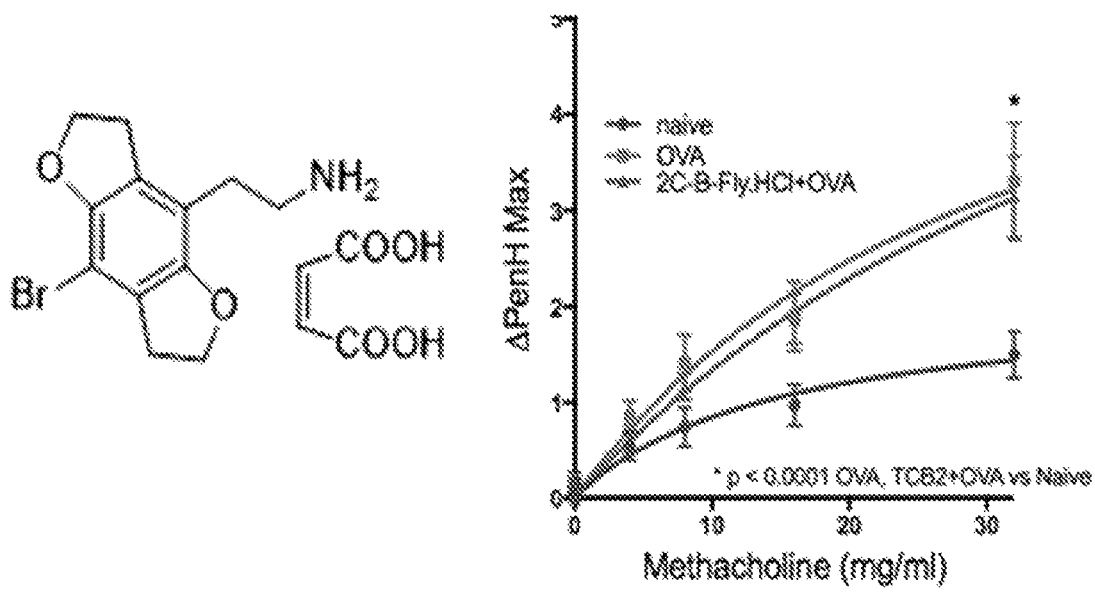
Figure 2E:
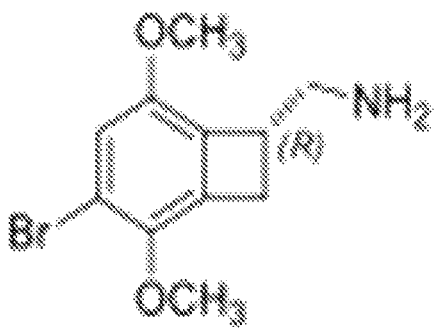
Figure 2E:
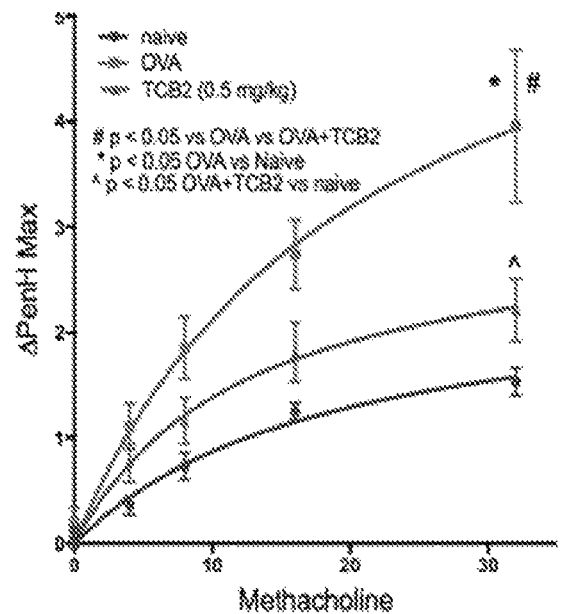
Figure 2F:
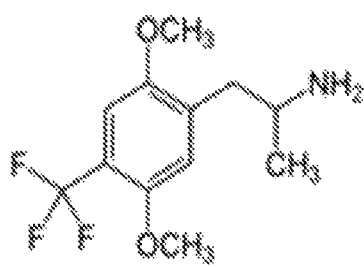
Figure 2F:
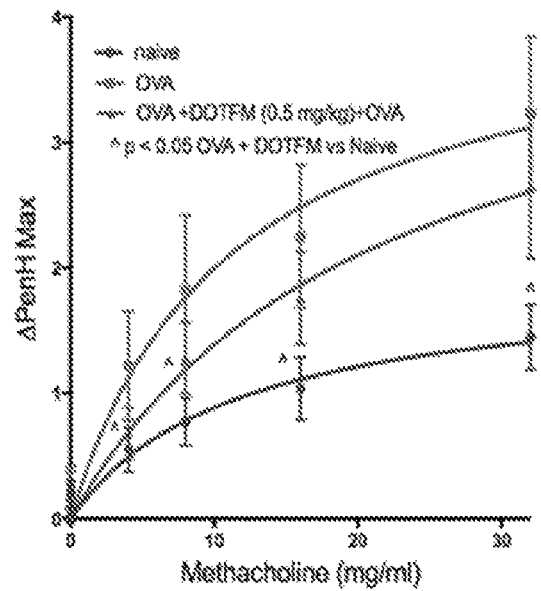
Figure 2G:
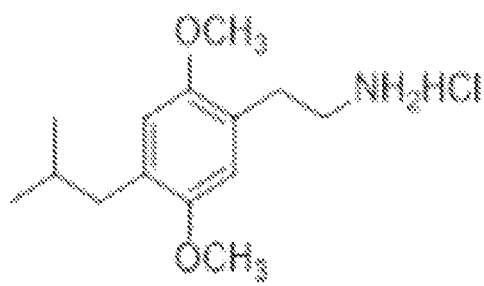
Figure 2G:
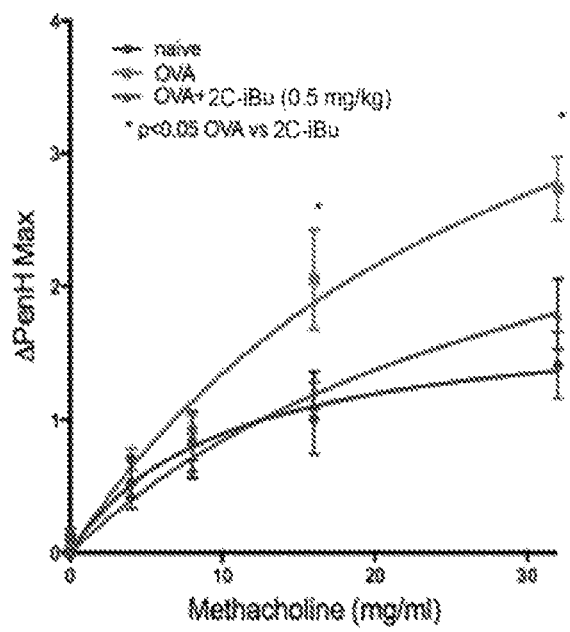

As shown in FIG. 2A, treatment with (R)-DOI demonstrated a full efficacy at preventing AHR, as measured by PenH in rats, in response to the allergen OVA. There is no statistical difference between the PenH values between naive (blue line) and (R)-DOI+OVA (red line) groups. As shown in FIG. 2B, 25I-NBOMe, which contains a modification of the amino group compared to R-DOI, exhibited reduced potency. Although 25I-NBOMe reduced PenH, PenH was significantly elevated over naive controls. As shown in FIG. 2C, altering the 4-position of the iodine in R-DOI to a bromine (thereby obtaining DOB) did not reduce potency. However, cyclizing the 2,5, dimethoxys and removing the alpha carbon reduced potency (FIG. 2D), as did cyclizing and rigidifying the side chain to obtain TCB-2 (FIG. 2E). Although TCB-2 reduced PenH, it was still significantly elevated over naive controls. As shown in FIG. 2F, replacement of the 4 position with trifluoromethyl eliminated efficacy. There was no statistical difference between the OVA and drug+OVA group in terms of PenH values. FIG. 2G shows that removal of the alpha carbon and placement of isobutyl at the 4-position to obtain 2C-iBu did not result in a decrease in efficacy compared to (R)-DOI. This result is representative of a fully efficacious anti-inflammatory effect to block bronchial inflammation that would otherwise elicit an increased response to methacholine.

A summary of the efficacy of various DOx and 2Cx compounds at 0.5 mg/kg dosage in rats at preventing AHR is provided in FIG. 3. Area under the curve of PenH values (PenH-AUC) in response to incremental doses of metacholine were calculated for each testing groups, naïve, OVA treated, and OVA+DRUG treated animals. A reduction in PenH-AUC values of more than 75% of the control values (OVA alone) was annotated as a strong efficacy. A moderate efficacy was 25-75% inhibition, and a lower than 25% inhibition was annotated as inactive. Additional to this information are provided the relative to R-DOI $EC_{50}$ values (ratio) of tested compounds in 5-$HT_{2A}$R heterologous cell-based calcium transient assay. Additionally provided are the estimated ratios of psychoactive doses in humans of each compound, relative to R-DOI. FIG. 3 illustrates the non-correlative nature of the therapeutic efficacy of the phenylethylamines class of compounds against inflammatory-mediated allergen-induced AHR and the reported evidences of the dose necessary for psychoactive disturbances experienced with these compounds in humans or the potency and strength of these compounds to the 5-$HT_{2A}$R in calcium transients assays.

Figure 4:
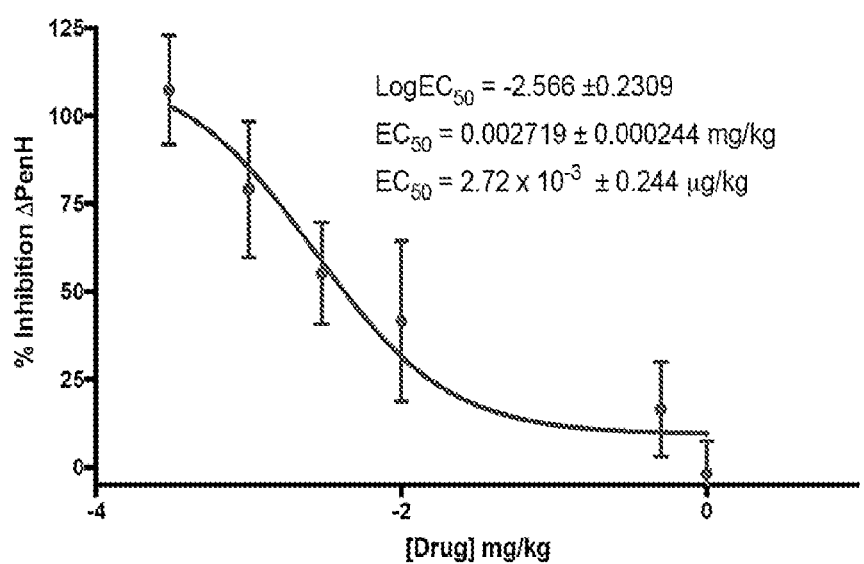
FIG. 4 is a dose response curve showing % inhibition of ΔPenh as a function of 2C-iBu concentration in the rat OVA allergic asthma model.

Inhibition of ΔPenh as a function of 2C-iBu concentration was studied by nebulization nose-only administration of 2C-iBu to male adult Brown Norway rats as described above. Results are shown in FIG. 4. Area under the curve for each treatment group at a given dose of 2C-iBu for ΔPenh is plotted on the Y-axis versus concentration of 2C-iBu on the X-axis. The $ED_{50}$ was 0.0027 mg/kg, equally as potent as (R)-DOI. Together, results shown in this example indicate that that 2C-iBu exhibits similar potency as (R)-DOI.

Example 4. Behavioral Studies

The head twitch response (HTR) can be used as a behavioral proxy in rodents for human hallucinogenic effects, because it can reliably distinguish hallucinogenic and non-hallucinogenic 5-$HT_{2A}$ receptor agonists. Similar to the discriminative stimulus effects of hallucinogens, the HTR serves as a behavioral readout of 5-$HT_{2A}$ activation and can be used to compare the in vivo potencies of 5-$HT_{2A}$ receptor agonists. HTR studies were conducted with (R)-DOI and 2C-iBu in C57BL/6J mice.

Materials and Methods

The following methods were used to obtain the results reported in this example.

Animals

Male C57BL/6J mice (6-8 weeks old) obtained from Jackson Laboratories (Bar Harbor, ME, USA) were housed at up to four per cage in a climate-controlled room on a reverse-light cycle (lights on at 1900 h, off at 0700 h) and were provided with ad libitum access to food and water, except during behavioral testing. Testing was conducted between 1000 and 1800 h.

Drugs

Drug doses are based on the equivalent freebase weight. Test substances were dissolved in sterile isotonic saline and injected subcutaneously (SC) at a volume of 5 mL/kg.

Head Twitch Response Studies

The HTR was assessed using a head-mounted magnet and a magnetometer detection coil, according to known methods. Briefly, mice were anesthetized, a small incision was made in the scalp, and a small neodymium magnet was attached to the dorsal surface of the cranium using dental cement. Following a two-week recovery period, HTR experiments were carried out in a well-lit room with at least seven days between sessions to avoid carryover effects. Test compounds were injected immediately prior to testing. Mice were injected with drug or vehicle and then HTR activity was recorded in a glass cylinder surrounded by a magnetometer coil. Coil voltage was low-pass filtered (2-10 kHz cutoff frequency), amplified, and digitized (20 kHz sampling rate) using a Powerlab/8SP with LabChart v 7.3.2 (ADInstruments, Colorado Springs, CO, USA), then filtered off-line (40-200 Hz band-pass). Head twitches were identified manually based on the following criteria: 1) sinusoidal wavelets; 2) evidence of at least three sequential head movements (usually exhibited as bipolar peaks) with frequency 40 Hz; 3) amplitude exceeding the level of background noise; 4) duration <0.15 s; and 5) stable coil voltage immediately preceding and following each response.

Experimental Design and Data Analysis

Experiment 1. Five groups of mice (n=6/group, 30 total) were treated with vehicle or R-DOI (0.1, 0.3, 1, or 3 mg/kg) and HTR activity was assessed for 30 minutes. Experiment 2. Five groups of mice (n=6-7/group, 34 total) were treated with vehicle or 2C-iBu (0.3, 1, 3, or 10 mg/kg) and HTR activity was assessed for 30 minutes. Experiment 3. Two groups of mice (n=7/group, 14 total) were treated with R-DOI (1 mg/kg) or 2C-iBu (3 mg/kg) and HTR activity was assessed for 210 minutes.

For Experiment 1 and Experiment 2, the entire thirty-minute recordings were examined for head twitches, head twitch counts were analyzed using one-way analyses of variance (ANOVA). In addition, HTR counts were analyzed in two-minute time blocks using one-way ANOVAs, with time as a repeated measure. Post hoc pairwise comparisons between selected groups were performed using Tukey's studentized range method. Significance was demonstrated by surpassing an α-level of 0.05.

Median effective doses ($ED_{50}$ values) and 95% confidence intervals (95% CI) were calculated by nonlinear regression (Prism 7.00, GraphPad Software, San Diego, CA, USA). A Gaussian distribution was used to fit biphasic HTR dose-response data:

$$E = \text{Baseline} + \text{Range} \times e^{-\left[\frac{\log\,[A]-midA}{slope}\right]^2}$$

$$midA = \log ED_{50} + slope\sqrt{-\ln\,(0.5)}$$

In these equations, E is the drug effect, Baseline is the response in the control group, Range is the distance from Baseline to the top of the curve, [A] is the dose of the drug, and midA is the logarithm of the dose corresponding to the top of the curve. To determine whether potency differences exist between individual compounds, $ED_{50}$ values were compared using an extra-sum-of-squares F-test. Significance was demonstrated by surpassing an α-level of 0.05.

For Experiment 3, HTR counts were examined in 5-min time blocks. To determine the half-life of drug responses, the descending phase of the data was fitted with a one-phase exponential decay function. The responses produced by R-(−)-DOI (1 mg/kg) or ELEU02 were analyzed using one-way ANOVA, with time as a repeated measure. Post hoc pairwise comparisons between groups were performed using Sidak's multiple comparisons test. Significance was demonstrated by surpassing an α-level of 0.05.

Results

Experiment 1

TABLE 6

| HTR induced by R-DOI | | | |
|---|---|---|---|
| Dose (mg/kg) | Mean | SEM | N |
| 0 | 8.7 | 1.1 | 6 |
| 0.1 | 46.5 | 4.4 | 6 |
| 0.3 | 78.8** | 10.6 | 6 |
| 1 | 128.0** | 13.2 | 6 |
| 3 | 116.0** | 24.1 | 6 |

** $p < 0.01$ vs. vehicle control, Tukey's test.

Figure 5A:
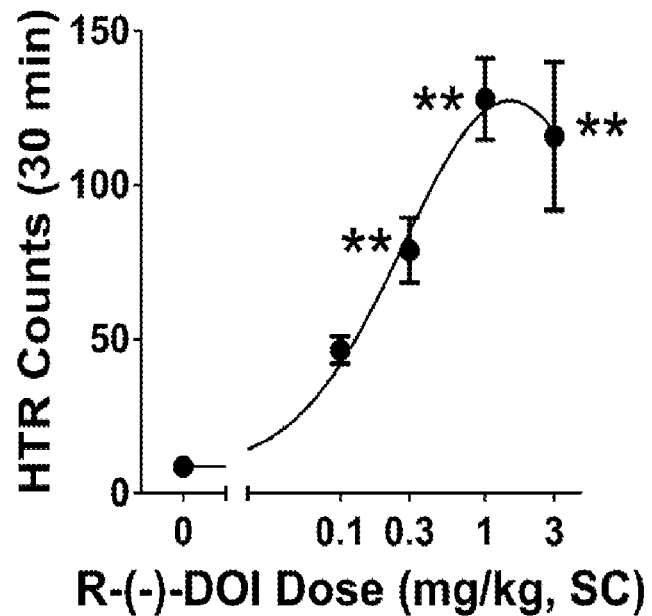
FIG. 5A is a graph showing the effect of R-DOI on the head twitch response (HTR). Data are presented as group means±SEM for the entire thirty-minute test session. Drug doses refer to the equivalent freebase weight. **$p<0.01$, significant difference from vehicle control group (Tukey's test).

Administration of R-DOI produced a dose-dependent increase in HTR counts (F(4,25)=13.70, p<0.0001; FIG. 5A and Table 6). The HTR induced by R-DOI followed an inverted-U-shaped dose-response function, with the peak response occurring after administration of 1 mg/kg (128.0±13.2 [mean±SEM] counts/30 min).

R-DOI induced the HTR with an $ED_{50}$ of 0.20 (95% CI 0.11-0.35) mg/kg. Based on molar mass, R-DOI has an $ED_{50}$ of 0.63 (95% CI 0.35-1.10) μmol/kg. Interestingly, when R-(−)-DOI is administered IP under otherwise identical experimental conditions, it induces the HTR with an $ED_{50}$ of 0.66 (95% CI 0.47-0.93) μmol/kg. Comparison of the $ED_{50}$ values using an extra-sum-of-squares F-test confirmed that the potency of R-DOI is not significantly influenced by its route of administration (F(1,52)=0.03, p=0.87).

Figure 5B:
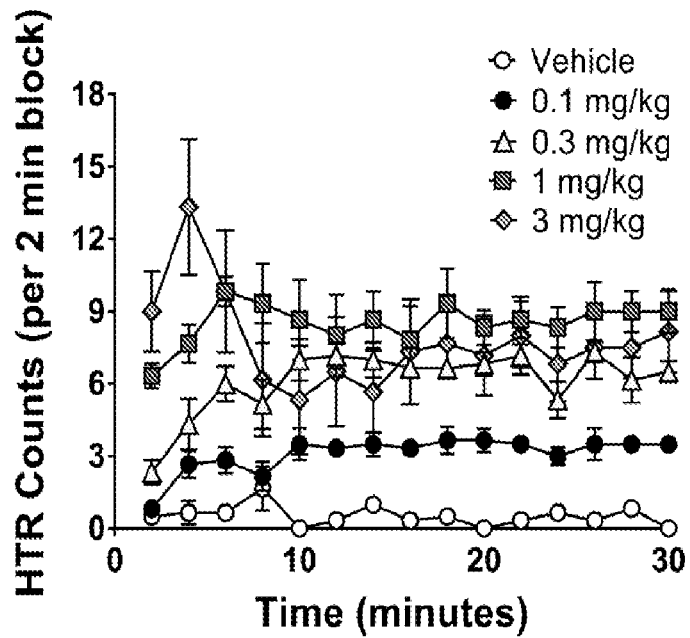
FIG. 5B is a graph showing the results of a time-course study of the HTR induced by R-DOI. Data are presented as group means±SEM during two-minute time blocks. Drug doses refer to the equivalent freebase weight.

The response to R-DOI was also analyzed in two-minute time blocks. As shown in FIG. 5B, the response to R-DOI was time-dependent (drug×time: F(56,350)=2.93, p<0.0001). The interval between injection and maximal effect was inversely proportional to the dosage of R-DOI. The maximal response occurred 24-26 minutes after administration of 0.3 mg/kg, 4-6 minutes after administration of 1 mg/kg, and 2-4 minutes after administration of 3 mg/kg.

Experiment 2

TABLE 7

| HTR induced by 2C-iBu. | | | |
|---|---|---|---|
| Dose (mg/kg) | Mean | SEM | N |
| 0 | 6.6 | 1.6 | 7 |
| 0.3 | 30.8 | 3.7 | 6 |
| 1 | 74.4** | 4.9 | 7 |
| 3 | 111.1** | 4.7 | 7 |
| 10 | 43.4* | 14.8 | 7 |

* $p < 0.05$,
** $p < 0.01$ vs. vehicle control, Tukey's test.

Figure 6A:
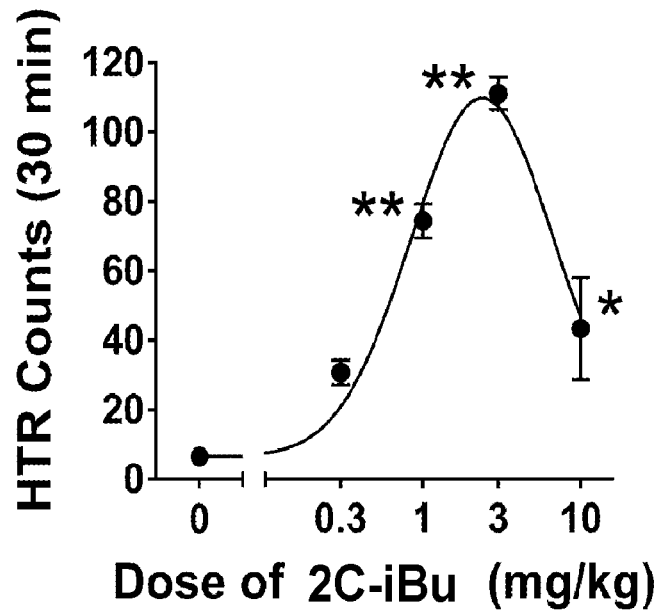
FIG. 6A is a graph showing the effect of 2C-iBu on HTR. Data are presented as group means±SEM for the entire thirty-minute test session. Drug doses refer to the equivalent freebase weight. *$p<0.05$, **$p<0.01$, significant difference from vehicle control group (Tukey's test).

Administration of 2C-iBu produced a dose-dependent increase in HTR counts (F(4,29)=28.36, p<0.0001; FIG. 6A). Similar to R-DOI, the HTR induced by 2C-iBu followed an inverted-U-shaped dose-response function, with the peak response occurring after administration of 3 mg/kg (111.1±4.7 counts/30 min).

2C-iBu induced the HTR with an $ED_{50}$ of 0.70 (95% CI 0.52-0.93) mg/kg. Based on molar mass, 2C-iBu has an $ED_{50}$ of 2.17 (95% CI 1.63-2.89) μmol/kg, meaning that it has ~3-fold lower behavioral potency than R-DOI. An extra-sum-of-squares F-test confirmed that 2C-iBu is significantly less behaviorally potent than R-DOI (F(1,58)=12.92, p=0.0007).

Figure 6B:
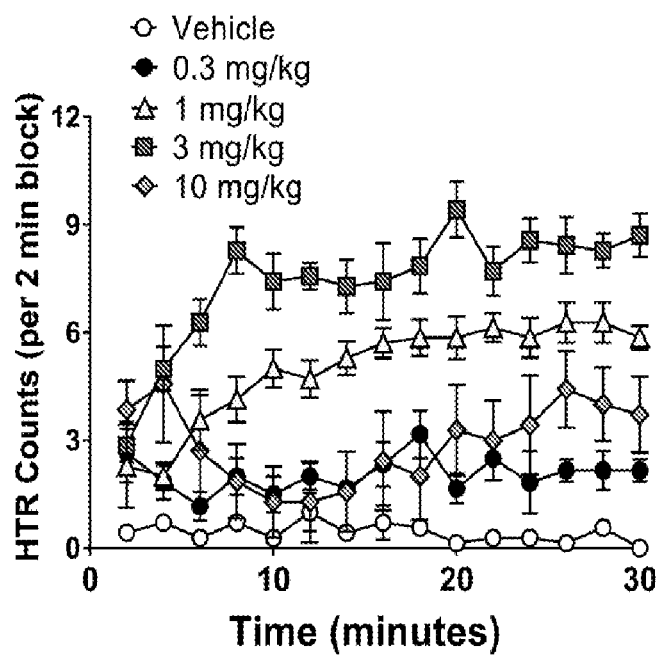
FIG. 6B is a graph showing the results of a time-course study of the HTR induced by 2C-iBu. Data are presented as group means±SEM during two-minute time blocks. Drug doses refer to the equivalent freebase weight.

The response to 2C-iBu was also analyzed in two-minute time blocks. As illustrated in FIG. 6B, the response to 2C-iBu was time-dependent (drug×time: F(56,406)=3.80, p<0.0001). The interval between injection and maximal effect was inversely proportional to the dosage of 2C-iBu. The maximal response occurred 24-28 minutes after administration of 1 mg/kg, 18-24 minutes after administration of 3 mg/kg, and 2-4 minutes after administration of 10 mg/kg.

Experiment 3

Next, the time course of the responses produced by R-DOI and 2C-iBu was characterized. For this experiment, mice were treated with maximally-effective doses of R-DOI (1 mg/kg SC) and 2C-iBu (3 mg/kg SC), and HTR activity was monitored continuously for 210 minutes.

Figure 7:
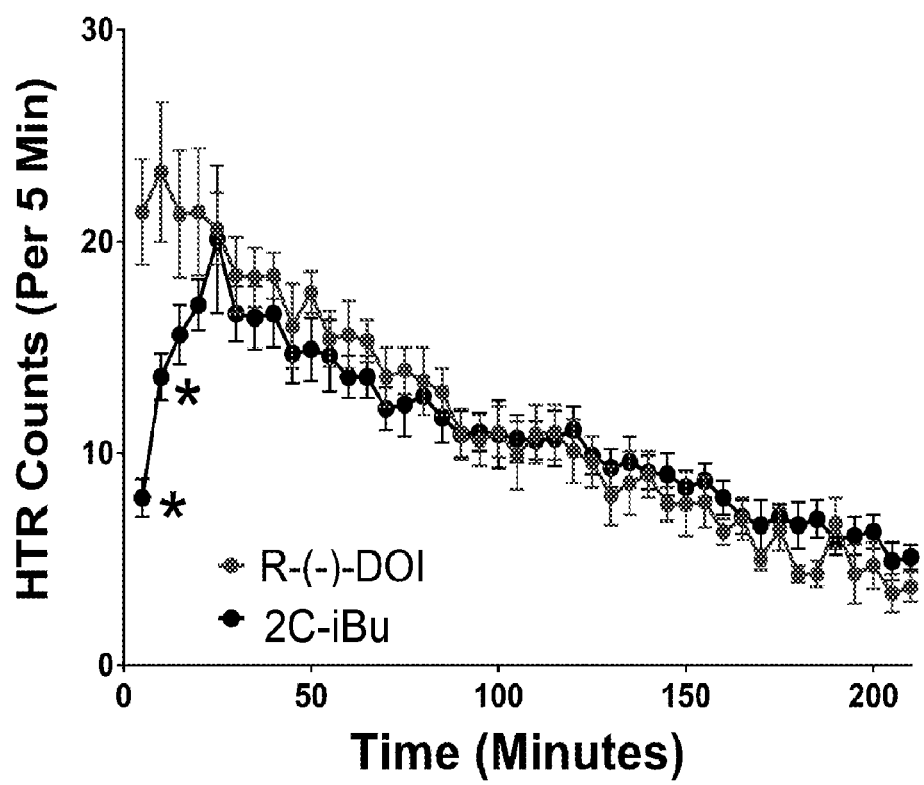
FIG. 7 is a graph showing the results of a time-course study of the HTR induced by 1.0 mg/kg R-DOI and 3.0 mg/kg 2C-iBu. Data are presented as group means±SEM during five-minute time blocks. Drug doses refer to the equivalent freebase weight. *$p<0.01$, significant difference between groups, (Sidak's multiple comparisons test).

The HTR induced by 1 mg/kg R-DOI peaked 5-10 min after administration (23.3±3.5 counts/5 min) and then gradually decreased over the remainder of the test session (FIG. 7). Fitting the data after the peak with a one-phase exponential decay function showed that the response had a half-life of 84.64 min (95% CI: 77.65-93.0 min; $r^2$=0.684).

The HTR induced by 3 mg/kg 2C-iBu peaked 20-25 min after administration (20.1±3.5 counts/5 min) and then gradually decreased over the remainder of the test session (FIG. 7). Fitting the data after the peak with a one-phase exponential decay function showed that the response had a half-life of 111.4 min (95% CI: 100.1-125.4 min; $r^2$=0.5709).

In addition to analyzing the time-course of the responses produced by R-DOI and 2C-iBu, we also compared their effects directly. Although there was not a main effect of drug treatment (F(1,12)=0.33, p=0.58), there was a main effect of time (F(41,192)=39.55, p<0.0001) and a significant interaction between drug treatment and time (F(41,492)=4.36, p<0.0001). Post hoc pairwise comparisons showed that there was only a significant difference between the effects of R-DOI and 2C-iBu during the first and second five-minute time blocks (p<0.0001, Sidak's multiple comparisons test).

These data demonstrate that 2C-iBu was about three-times less potent than R-DOI at eliciting head twitch response in a rodent model of 5-$HT_{2A}$ receptor-mediated psychoactivity. In addition, 2C-iBu demonstrated a significant delay in time to peak response in eliciting the head twitch behavior compared to R-DOI. Example 3, on the other hand, demonstrated that therapeutic potency of 2C-iBu was similar to R-DOI at reducing AHR in the rodent asthmatic inflammatory model. Thus, while 2C-iBu retains the therapeutic properties of interest in a disease model of inflammation, these results indicate that this compound does not share the same propensity as R-DOI in eliciting undesirable psychoactive effects.

Example 5. 5-HT Receptor Binding Studies

This example describes testing of R-DOI and 2C-iBu in binding assays of various 5-HT receptors. Radioligand binding was assessed at equilibrium, using the ligands indicated in Table 8, at recombinantly expressed human receptors from membrane preparations using standard conditions at Cerep Eurofins Discovery and gold standard filtration methods, in accordance with generally accepted methodologies as described in Auld et al. (Receptor Binding Assays for HTS and Drug Discovery. 2012. In: Sittampalam et al., editors. Assay Guidance Manual [Internet], Bethesda (Md.): Eli Lilly & Company and the National Center for Advancing Translational Sciences; 2004). Each test compound was titrated and tested at several concentrations under competitive binding conditions to determine the half maximal inhibitory concentration (IC50) and its apparent binding affinity (equilibrium dissociation constant (Ki). The IC50 values (concentration causing a half-maximal inhibition of control specific binding) and Hill coefficients (nH) were determined by non-linear regression analysis of the competition curves generated with mean replicate values using Hill equation curve fitting. This analysis was performed using software developed at Cerep (Hill software) and validated by comparison with data generated by the commercial software SigmaPlot® 4.0 for Windows® (©1997 by SPSS Inc.). The inhibition constants (Ki) were calculated using the Cheng Prusoff equation. pKi values were calculated as the negative logarithm to base 10 of the equilibrium dissociation constant, Ki in molar concentration units and are listed below in Table 8. Table 9 shows the example pIC50 of one reference ligand for each receptor tested under generally similar experimental conditions. Generally, the pKi values of both tested compounds indicate a greater affinity to their primary or co-primary receptor target(s) than the endogenous ligand serotonin. The specificity of R-1301 in regards to apparent affinity to 5-HT receptors was_2A>_2C>_2B>>_1A=_1B. The specificity of 2C-iBu in regards to the apparent affinity to the 5-HT receptors was _2C>_2A>_2B>_1A=_1B=_1C>_7>_6.

TABLE 8

| ASSAY | (2C-iBu) pKi | (R-DOI) pKi |
|---|---|---|
| 5-HT1A (h) (agonist radioligand, [3H]8-OH-DPAT) | 7.1 | 5.9 |
| 5-HTB (antagonist radioligand, [125I]CYP) | 7.3 | 5.6 |
| 5-HT1D (agonist radioligand, [3H]serotonin) | 7.2 | Not tested |
| 5-HT2A (h) (agonist radioligand, [125I]($\pm$)DOI) | 8.9 | 10.4 |
| 5-HT2B (h) (agonist radioligand, [125I]($\pm$)DOI) | 7.8 | 8.6 |
| 5-HT2C (h) (agonist radioligand, [125I]($\pm$)DOI) | 9.6 | 9.2 |
| 5-HT6 (h) (agonist radioligand, [3H]LSD) | 5.9 | Not tested |
| 5-HT7 (h) (agonist radioligand, [3H]LSD) | 6.5 | Not tested |

TABLE 9

| ASSAY | Ligand | pIC50 |
|---|---|---|
| 5-HT1A (h) (agonist radioligand, [3H]8-OH-DPAT) | 8-OH-DPAT | 8.7 |
| 5-HTB (antagonist radioligand, [125I]CYP) | serotonin | 6.7 |
| 5-HT1D (agonist radioligand, [3H]serotonin) | serotonin | 8.7 |
| 5-HT2A (h) (agonist radioligand, [125I]($\pm$)DOI) | serotonin | 8 |
| 5-HT2B (h) (agonist radioligand, [125I]($\pm$)DOI) | serotonin | 8.7 |
| 5-HT2C (h) (agonist radioligand, [125I]($\pm$)DOI) | serotonin | 8.6 |
| 5-HT6 (h) (agonist radioligand, [3H]LSD) | serotonin | 6.8 |
| 5-HT7 (h) (agonist radioligand, [3H]LSD) | serotonin | 9.4 |

Example 6. Toxicity Studies of R-DOI and 2C-iBu

In vitro protein binding, absorption, and microsome intrinsic clearance studies were conducted to compare a number of in vitro ADME/tox metrics between R-DOI and 2C-iBu. Each assay was standardized and methods were validated to meet criteria acceptance of non-GLP studies in drug development and in accordance of generally accepted methodology as described in Chung et al. (In Vitro and In Vivo Assessment of ADME and PK Properties During Lead Selection and Lead Optimization—Guidelines, Benchmarks and Rules of Thumb. 2015; In: Sittampalam et al. Assay Guidance Manual [Internet]. Bethesda (Md.): Eli Lilly & Company and the National Center for Advancing Translational Sciences; 2004).

In vitro protein binding assays were conducted using test compound (R-DOI or 2C-iBu) in human plasma. R-DOI and 2C-iBu were each tested at a concentration of $1.0 \times 10^{-5}$ M. Results are shown in Table 10, below.

TABLE 10

Protein binding assay results

| | % Protein bound | | | % Recovery | | |
|---|---|---|---|---|---|---|
| | 1st | 2nd | Mean | 1st | 2nd | Mean |
| R-DOI | 47.5 | 49.6 | 49 | 126 | 126 | 126 |
| 2C-iBu | 73.7 | 74.5 | 74 | 107 | 105 | 106 |

In vitro absorption assays were conducted using test compound (R-DOI or 2C-iBu) incubated with Caco-2 cells at pH 6.5/7.4. R-DOI and 2C-iBu were each tested at a concentration of $1.0 \times 10^{-5}$ M. Results are shown in Table 11, below.

TABLE 11

Absorption assay results

| | Permeability ($10^{-8}$ cm/s) | | | % Recovery | | |
|---|---|---|---|---|---|---|
| | 1st | 2nd | Mean | 1st | 2nd | Mean |
| | A-B Permeability | | | | | |
| R-DOI | 23.66 | 23.20 | 23.4 | 72 | 72 | 72 |
| 2C-ibu | 10.90 | 10.57 | 10.7 | 45 | 48 | 46 |
| | B-A Permeability | | | | | |
| R-DOI | 19.15 | 19.27 | 19.2 | 87 | 88 | 87 |
| 2C-ibu | 7.87 | 7.92 | 7.9 | 70 | 72 | 71 |

In vitro metabolism assays were conducted to test for intrinsic clearance using test compound (R-DOI or 2C-iBu) incubated at various times (0 minutes, 15 minutes, 30 minutes, 45 minutes, and 60 minutes) with human liver microsomes. R-DOI and 2C-iBu were each tested at a concentration of $1.0\times10^{-7}$ M. Results are shown in Table 12, below.

TABLE 12

In vitro metabolism results

| | Incubation time | % Compound Remaining | | | Half-life (minutes) | | | |
| --- | --- | --- | --- | --- | --- | --- | --- | --- |
| | | 1st | 2nd | Mean | 1st | 2nd | Mean | Clint |
| R-DOI | 0 | 100 | 100 | 100 | 138.7 | 187.6 | >60 | <115.5 |
| | 15 | 90.0 | 101.6 | 96 | | | | |
| | 30 | 79.6 | 105.3 | 92 | | | | |
| | 45 | 77.0 | 82.1 | 80 | | | | |
| | 60 | 74.3 | {91.4} | 74 | | | | |
| 2C-iBu | 0 | 100 | 100 | 100 | >60 | 1016.4 | >60 | <115.5 |
| | 15 | 91.0 | {126.7} | 91 | | | | |
| | 30 | 113.6 | 114.2 | 114 | | | | |
| | 45 | 105.3 | 106.5 | 106 | | | | |
| | 60 | 94.1 | 94.2 | 94 | | | | |

In general, both compounds had full solubility at the maximal tested concentrations of 200 micromolar in PBS and simulated intestinal fluid aqueous environments. 2C-iBu displayed a decreased hydrophilic profile in comparison to R-DOI with increased log D at physiological pH from 1.04 for R-DOI to 1.64 for 2C-iBu. This differential in the physico-chemical properties could be one of the drivers in the observed increased plasma protein binding capability of 2Ci-Bu in comparison to R-DOI and the moderate changes in the Caco-2 A-B/B-A permeability profiles. Both R-DOI and 2C-iBu were metabolically stable compounds with a Clint <115.5 in the human liver microsomes intrinsic clearance assay.

Example 7. Proof of Concept Studies for Treatment of Inflammatory Arthritis

Collagen-induced arthritis is an animal model of human rheumatoid arthritis. Mice are immunized with type II collagen (CII) (e.g., bovine CII). This model recapitulates many of the innate and adaptive immune mechanisms that characterize human rheumatoid arthritis, and has been used to test treatments subsequently developed as human therapies.

Arthritis is induced in C57/Bl6 mice in three steps. Mice are immunized on day 0 with bovine CII in complete Freund's adjuvant, administered subcutaneously (s.c.). On day 21, a second immunization with CII suspended in incomplete Freund's adjuvant is administered s.c. Lastly, on day 24, 25 µg of lipopolysaccharide is administered via intraperitoneal injection.

Mice are dosed twice per week via tail vein injection of a 2C compound at a dose that has been verified as non-behaviorally potent, e.g., according to methods described herein, at the dosage and frequency administered. Control mice are not immunized with CII and received no treatment or placebo. Treatment is begun after 10% to 30% of mice develop arthritis.

Mice are evaluated by cumulative disease score daily. Mice are weighed once or twice per week for the first three weeks, and paw thickness is measured twice per week. Blood, lymph nodes, spleen, and joints are harvested for histopathology and immunological analyses, including titer of anti-CII antibodies in blood and other inflammatory markers expressed by cells and circulating in blood, such as inflammatory cytokines.

Mice receiving the 2C compound exhibit a lower cumulative score, a lower frequency of arthritic limbs, and a lower average paw thickness, relative to control mice. Mice receiving the 2C compound also have lower levels of anti-CII antibodies (e.g., IgG2a) and pro-inflammatory markers, such as activated immune cells and circulating inflammatory cytokines, relative to control mice.

Example 8. Proof of Concept Studies for Treatment of Multiple Sclerosis

Experimental autoimmune encephalomyelitis (EAE) is a mouse model of multiple sclerosis, which shares many pathogenic underpinnings with a broad range of autoimmune disorders. This Example outlines the treatment of EAE with 2C compounds.

EAE is induced in C57BL/6 mice by subcutaneously injecting 200 µg $MOG_{35-55}$ in complete Freund's adjuvant. In addition, 200 ng of pertussis toxin is administered intraperitoneally (i.p.) on days 0 and 2.

2C compound is administered intravenously in an amount and at a frequency verified as non-behaviorally potent, e.g., using any of the methods described herein. Mice are monitored daily, beginning on day 10 and continuing through day 24, for clinical signs of EAE. EAE is scored as follows: 0, no sign of disease; 1, loss of tone in the tail; 2, hind limb paresis; 3, hind limb paralysis; 4, tetraplegia; and 5, moribund. The average score is calculated for each group of mice. At the conclusion of the experiment, brain, lymph node, and spleen are harvested, and the following experiments are performed to assess the immunologic effects of the 2C compounds:

Spleens are dissociated into single cell suspensions and stimulated with $MOG_{35-55}$ peptide at concentrations of 1, 10, or 100 µg/mL to measure immunological recall. Cell proliferation is measured after 72 hours using an MTT cell proliferation assay. Brain and spinal cord are harvested and dissociated into single-cell suspensions. T cells are isolated using magnetic beads, stained with antibodies against interleukin 17 (IL-17) and interferon gamma (IFNγ), and analyzed by flow cytometry.

Mice receiving sub-behavioral doses of the 2C compound exhibit a lower recall response to $MOG_{35-55}$ peptide relative to control mice, e.g., as characterized by lower cell proliferation using the MTT assay. T cells from brain and spinal cord tissues of mice receiving sub-behavioral doses of the 2C compound express lower amounts of inflammatory markers, such as IL-17 and IFNγ, relative to control mice.

Other Embodiments

All publications, patents, and patent applications mentioned in this specification are herein incorporated by reference to the same extent as if each independent publication or patent application was specifically and individually indicated to be incorporated by reference.

Although the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A compound of formula (I):

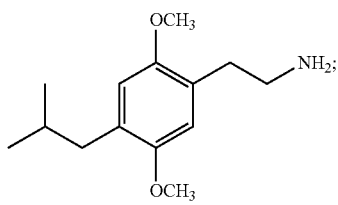

or a pharmaceutically acceptable acid addition salt or prodrug thereof.

2. A pharmaceutical composition comprising the compound of claim 1, and a pharmaceutically acceptable excipient.

3. A method of treating an inflammatory disorder in a subject in need thereof, the method comprising administering to the subject a therapeutically effective amount of the compound of claim 1.

4. The method of claim 3, wherein the compound is administered in an amount less than 20 µg/kg body weight.

5. The method of claim 3, wherein the compound is administered orally, intranasally, or by inhalation at a frequency of one to three times per week.

6. The method of claim 3, wherein the inflammatory disorder is selected from the group consisting of asthma, chronic obstructive pulmonary disease, neuroinflammation, rheumatoid arthritis, atherosclerosis, psoriasis, type II diabetes, inflammatory bowel disease, Crohn's disease, multiple sclerosis, septicemia, and conjunctivitis.

7. A compound of formula (II):

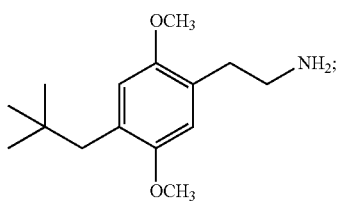

or a pharmaceutically acceptable acid addition salt or prodrug thereof.

8. A pharmaceutical composition comprising the compound of claim 7 and a pharmaceutically acceptable excipient.

9. A method of treating an inflammatory disorder in a subject in need thereof, the method comprising administering to the subject a therapeutically effective amount of the compound of claim 7.

10. The method of claim 9, wherein the compound is administered in an amount less than 20 µg/kg body weight.

11. The method of claim 9, wherein the compound is administered orally, intranasally, or by inhalation at a frequency of one to three times per week.

12. The method of claim 9, wherein the inflammatory disorder is selected from the group consisting of asthma, chronic obstructive pulmonary disease, neuroinflammation, rheumatoid arthritis, atherosclerosis, psoriasis, type II diabetes, inflammatory bowel disease, Crohn's disease, multiple sclerosis, septicemia, and conjunctivitis.

13. A compound of formula (III):

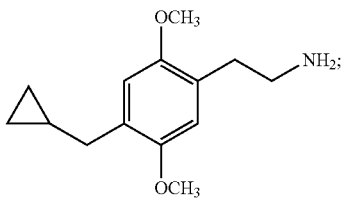

or a pharmaceutically acceptable acid addition salt or prodrug thereof.

14. A pharmaceutical composition comprising the compound of claim 13 and a pharmaceutically acceptable excipient.

15. A method of treating an inflammatory disorder in a subject in need thereof, the method comprising administering to the subject a therapeutically effective amount of the compound of claim 13.

16. The method of claim 15, wherein the compound is administered in an amount less than 20 µg/kg body weight.

17. The method of claim 15, wherein the compound is administered orally, intranasally, or by inhalation at a frequency of one to three times per week.

18. The method of claim 15, wherein the inflammatory disorder is selected from the group consisting of asthma, chronic obstructive pulmonary disease, neuroinflammation, rheumatoid arthritis, atherosclerosis, psoriasis, type II diabetes, inflammatory bowel disease, Crohn's disease, multiple sclerosis, septicemia, and conjunctivitis.

* * * * *